United States Patent
Linden et al.

(10) Patent No.: US 10,485,964 B2
(45) Date of Patent: Nov. 26, 2019

(54) IMPLANTABLE DUAL RESERVOIR ACCESS PORT

(71) Applicant: Medical Components, Inc., Harleysville, PA (US)

(72) Inventors: Christopher Linden, Allentown, PA (US); Raymond Bizup, Feasterville, PA (US); Cristian M. Ciuciu, Huntingdon Valley, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 15/212,725

(22) Filed: Jul. 18, 2016

(65) Prior Publication Data
US 2016/0325083 A1 Nov. 10, 2016

Related U.S. Application Data

(63) Continuation of application No. 13/092,892, filed on Apr. 22, 2011.
(Continued)

(51) Int. Cl.
*A61M 39/02* (2006.01)
*A61M 39/10* (2006.01)
(Continued)

(52) U.S. Cl.
CPC ........ *A61M 39/0208* (2013.01); *A61M 5/007* (2013.01); *A61M 39/02* (2013.01);
(Continued)

(58) Field of Classification Search
CPC ...... A61M 39/0208; A61M 2039/0226; A61M 2039/0211; A61M 39/08; A61M 39/22;
(Continued)

(56) References Cited

U.S. PATENT DOCUMENTS

| | | |
|---|---|---|
| 2,260,454 A | 10/1941 | Hedeman |
| 2,854,030 A | 9/1958 | Schulthess |

(Continued)

FOREIGN PATENT DOCUMENTS

| | | |
|---|---|---|
| AU | 698034 | 10/1998 |
| BR | 112012027040 A2 | 7/2016 |

(Continued)

OTHER PUBLICATIONS

European Patent Office, Supplemental European Search Report, dated Oct. 29, 2014.
(Continued)

*Primary Examiner* — Bhisma Mehta
*Assistant Examiner* — William R Frehe

(57) ABSTRACT

A dual reservoir access port includes a base having proximal and distal fluid reservoirs. The fluid reservoirs each comprise a bottom and a side wall. A dual prong outlet stem projects from a distal end of the base and comprises a first prong and a second prong. A first fluid channel extends through the first prong to the distal reservoir, and a second fluid channel extends through the second prong to the proximal fluid reservoir. A puncture shield is disposed between at least a portion of the second fluid channel and the bottom of the distal fluid reservoir. A needle-penetrable septum is disposed atop of each of the fluid reservoirs. A cap is placed over and around the port base compressing and sealing the septa against the base. A locking collar may be placed over a dual lumen catheter to lock the catheter to the dual prong outlet stem.

14 Claims, 9 Drawing Sheets

Related U.S. Application Data

(60) Provisional application No. 61/327,249, filed on Apr. 23, 2010.

(51) Int. Cl.
 *A61M 5/00* (2006.01)
 *A61M 39/00* (2006.01)

(52) U.S. Cl.
 CPC ........ *A61M 39/10* (2013.01); *A61M 39/1011* (2013.01); *A61M 2039/0036* (2013.01); *A61M 2039/0054* (2013.01); *A61M 2039/0072* (2013.01); *A61M 2039/0081* (2013.01); *A61M 2039/0211* (2013.01); *A61M 2039/0223* (2013.01); *A61M 2039/0226* (2013.01); *A61M 2205/582* (2013.01); *A61M 2205/60* (2013.01); *A61M 2207/00* (2013.01)

(58) Field of Classification Search
 CPC .................. A61J 15/0026; A61J 1/1475; A61J 2001/1481; A61J 2001/1487; A61J 15/0092
 See application file for complete search history.

(56) References Cited

U.S. PATENT DOCUMENTS

| | | | |
|---|---|---|---|
| 3,891,250 A | 6/1975 | Oetiker | |
| 3,938,237 A | 2/1976 | Dunz | |
| 3,944,261 A | 3/1976 | Reed et al. | |
| 3,948,546 A | 4/1976 | Welsby et al. | |
| 4,116,589 A * | 9/1978 | Rishton | A61M 1/1098 417/384 |
| 4,116,789 A | 9/1978 | King | |
| 4,537,183 A | 8/1985 | Fogarty | |
| 4,635,972 A | 1/1987 | Lyall | |
| 4,692,146 A | 9/1987 | Hilger | |
| 4,693,707 A | 9/1987 | Dye | |
| 4,900,312 A | 2/1990 | Nadeau | |
| 4,903,995 A | 2/1990 | Blenkush et al. | |
| 4,915,690 A | 4/1990 | Cone et al. | |
| 4,929,236 A | 5/1990 | Sampson | |
| D309,774 S | 8/1990 | Lewis | |
| 4,946,200 A | 8/1990 | Blenkush et al. | |
| 5,041,098 A | 8/1991 | Loiterman et al. | |
| 5,167,638 A * | 12/1992 | Felix | A61M 39/0208 604/175 |
| 5,213,574 A | 5/1993 | Tucker | |
| D337,637 S | 7/1993 | Tucker | |
| D347,687 S | 6/1994 | Katzer et al. | |
| 5,360,407 A | 11/1994 | Leonard | |
| 5,387,192 A | 2/1995 | Glantz et al. | |
| 5,399,168 A | 3/1995 | Wadsworth, Jr. et al. | |
| D371,196 S | 6/1996 | Loffert | |
| 5,558,641 A | 9/1996 | Glantz et al. | |
| 5,562,618 A | 10/1996 | Cai et al. | |
| 5,613,945 A | 3/1997 | Cai et al. | |
| 5,632,729 A | 5/1997 | Cai et al. | |
| 5,637,102 A | 6/1997 | Tolkoff et al. | |
| 5,709,413 A * | 1/1998 | Salyers | F16L 33/223 285/219 |
| 5,743,873 A | 4/1998 | Cai et al. | |
| 5,792,104 A | 8/1998 | Speckman et al. | |
| 5,833,654 A * | 11/1998 | Powers | A61M 39/0208 604/93.01 |
| 5,931,801 A | 8/1999 | Burbank et al. | |
| 6,039,712 A * | 3/2000 | Fogarty | A61M 39/0208 604/175 |
| 6,086,555 A * | 7/2000 | Eliasen | A61M 39/0208 604/175 |
| 6,113,572 A | 9/2000 | Gailey et al. | |
| 6,213,973 B1 | 4/2001 | Eliasen et al. | |
| D450,115 S | 11/2001 | Bertheas | |
| 6,527,754 B1 | 3/2003 | Tallarida et al. | |
| 6,565,525 B1 | 5/2003 | Burbank et al. | |
| 6,641,177 B1 | 11/2003 | Pinciaro | |
| 7,163,531 B2 | 1/2007 | Seese et al. | |
| D546,440 S | 7/2007 | Burnside | |
| D556,153 S | 11/2007 | Burnside | |
| D562,443 S | 2/2008 | Zinn et al. | |
| D574,950 S | 8/2008 | Zawacki et al. | |
| D578,203 S | 10/2008 | Bizup | |
| 9,731,104 B2 | 8/2017 | Linden et al. | |
| 2002/0038953 A1 | 4/2002 | Mcnab et al. | |
| 2003/0181878 A1 | 9/2003 | Tallarida et al. | |
| 2004/0199129 A1 | 10/2004 | DiMatteo | |
| 2005/0171502 A1 | 8/2005 | Daly et al. | |
| 2005/0215960 A1 | 9/2005 | Girard et al. | |
| 2006/0058744 A1 | 3/2006 | Tallarida et al. | |
| 2006/0116648 A1 | 6/2006 | Hamatake | |
| 2006/0207601 A1 | 9/2006 | Nasir | |
| 2006/0224129 A1 | 10/2006 | Beasley et al. | |
| 2006/0247584 A1 | 11/2006 | Sheetz et al. | |
| 2006/0264898 A1 | 11/2006 | Beasley et al. | |
| 2007/0078416 A1 | 4/2007 | Eliasen | |
| 2007/0270770 A1 | 11/2007 | Bizup | |
| 2008/0103486 A1 | 5/2008 | Owens | |
| 2008/0140025 A1 | 6/2008 | Sheetz et al. | |
| 2008/0319398 A1 | 12/2008 | Bizup | |
| 2008/0319399 A1 | 12/2008 | Schweikert et al. | |
| 2008/0319405 A1 | 12/2008 | Bizup | |
| 2009/0099526 A1 | 4/2009 | Powley et al. | |
| 2009/0118683 A1 | 5/2009 | Hanson et al. | |
| 2009/0156928 A1 | 6/2009 | Evans et al. | |
| 2009/0204072 A1 | 8/2009 | Amin et al. | |
| 2009/0221976 A1 | 9/2009 | Linden | |
| 2009/0306606 A1 | 12/2009 | Lancette | |
| 2011/0264058 A1 | 10/2011 | Linden et al. | |
| 2016/0325084 A1 | 11/2016 | Linden et al. | |
| 2017/0197072 A1 | 7/2017 | Linden et al. | |

FOREIGN PATENT DOCUMENTS

| | | |
|---|---|---|
| CA | 2076920 A1 | 3/1993 |
| CA | 2181575 A1 | 7/1995 |
| CA | 2278035 A1 | 7/1998 |
| CA | 2289496 A1 | 11/1998 |
| CA | 2553536 A1 | 8/2005 |
| CA | 2796735 A1 | 10/2011 |
| DE | 19752692 A1 | 6/1998 |
| DE | 20103979 U1 | 7/2001 |
| EP | 0366814 A1 | 5/1990 |
| EP | 0537892 A1 | 4/1993 |
| EP | 0858814 A1 | 8/1998 |
| EP | 0930082 A2 | 7/1999 |
| EP | 2560726 A1 | 2/2013 |
| FR | 2586569 A1 | 3/1987 |
| FR | 2757407 A1 | 6/1998 |
| GB | 2178811 A | 2/1987 |
| JP | 56-80583 A | 7/1981 |
| JP | 2-29269 A | 1/1990 |
| JP | 9-508036 A | 8/1997 |
| MX | 353638 B | 1/2018 |
| WO | 93/17269 A1 | 9/1993 |
| WO | 95/19801 A1 | 7/1995 |
| WO | 9519200 A1 | 7/1995 |
| WO | 96/29112 A1 | 9/1996 |
| WO | 98/31417 A2 | 7/1998 |
| WO | 98/51366 A1 | 11/1998 |
| WO | 00/33901 A1 | 6/2000 |
| WO | 2005/072811 A1 | 8/2005 |
| WO | 2005/102442 A1 | 11/2005 |
| WO | 2006/096686 A1 | 9/2006 |
| WO | 2007/079024 A2 | 7/2007 |
| WO | 2011/133950 A1 | 10/2011 |

OTHER PUBLICATIONS

International Application No. PCT/US11/33686, International Search Report, dated Apr. 22, 2011, 2 pages.
International Application No. PCT/US11/33686, Written Opinion, dated Apr. 22, 2011, 6 pages.

(56) References Cited

OTHER PUBLICATIONS

Nonfinal Office Action issued in co-pending U.S. Appl. No. 15/212,765, 34 pages (dated May 26, 2017).
Final Office Action issued in co-pending U.S. Appl. No. 15/212,765, 22 pages (dated Sep. 22, 2017).
Nonfinal Office Action issued in co-pending U.S. Appl. No. 15/212,765, 19 pages (dated Mar. 15, 2018).
Non Final Office Action Received for U.S. Appl. No. 13/092,892, dated Feb. 17, 2015, 19 pages.
Final Office Action Received for U.S. Appl. No. 13/092,892, dated Jul. 10, 2015, 21 pages.
Non Final Office Action Received for U.S. Appl. No. 13/092,892, dated Feb. 26, 2016, 22 pages.
Final Office Action Received for U.S. Appl. No. 13/092,892, dated Jun. 15, 2016, 25 pages.
Notice of Allowance Received for U.S. Appl. No. 13/092,892, dated Apr. 12, 2017, 12 pages.
Final Office Action Received for U.S. Appl. No. 15/212,765, dated Sep. 4, 2018, 15 pages.
Office Action Received for Canadian Patent Application No. CA 2,796,735, dated Dec. 22, 2016, 6 pages.
Office Action Received for Canadian Patent Application No. CA 2,796,735, dated Sep. 12, 2017, 5 pages.
Office Action Received for Canadian Patent Application No. CA 2,796,735, dated Jun. 6, 2018, 3 pages.
Office Action Received for European Patent Application No. EP 11772827.9, dated Jul. 6, 2016, 3 pages.
International Preliminary Report on Patentability Received for PCT Patent Application No. PCT/US2011/033686, dated Nov. 1, 2012, 8 pages.

* cited by examiner

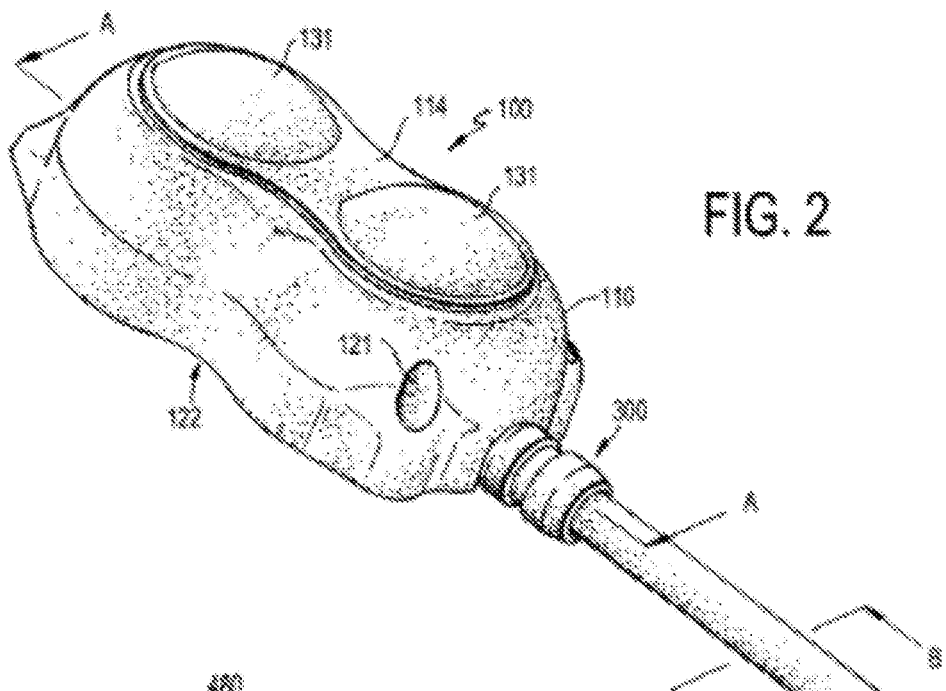
FIG. 2
FIG. 8
FIG. 3
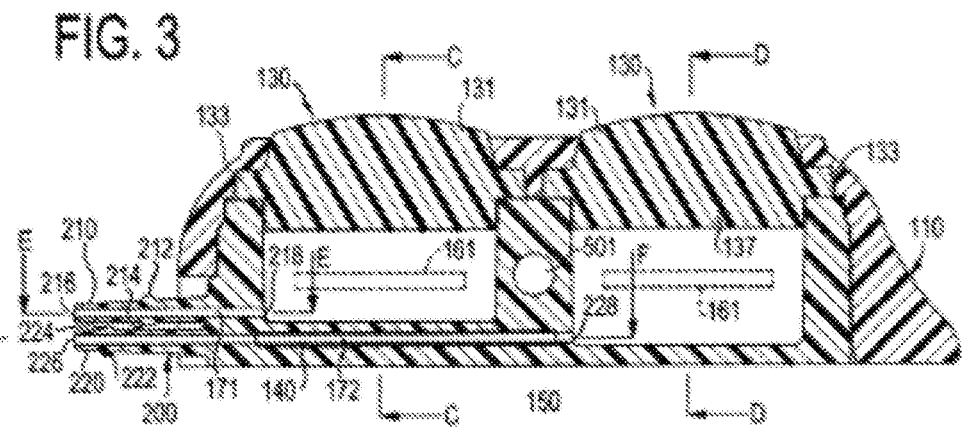

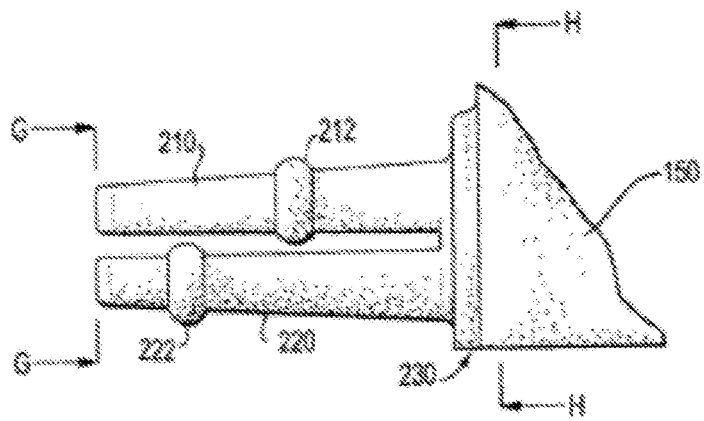
FIG. 6
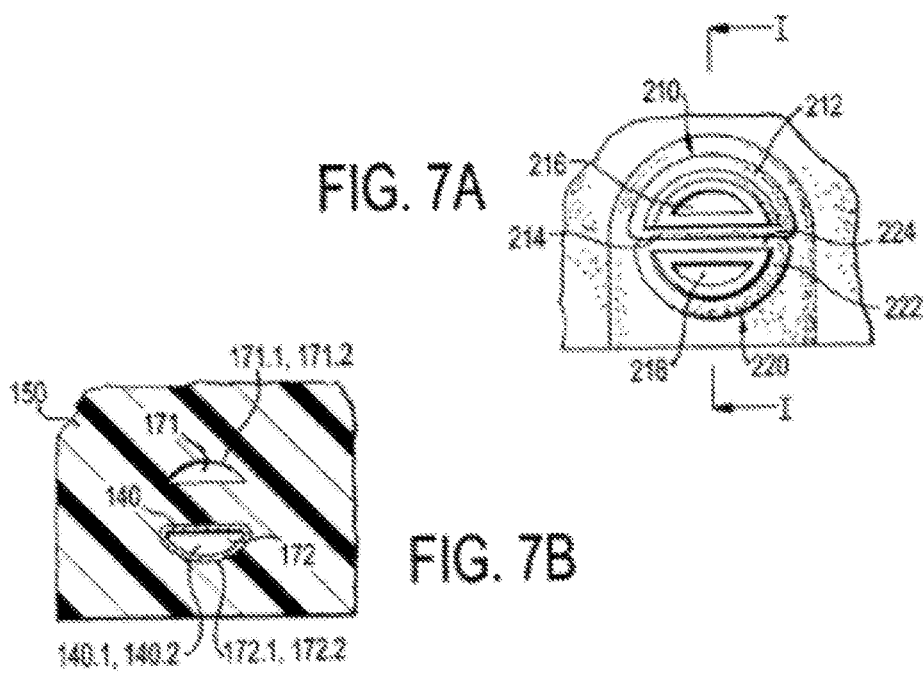
FIG. 7A
FIG. 7B
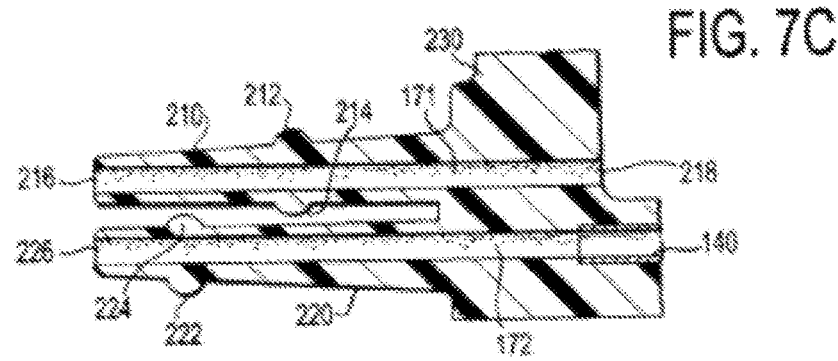
FIG. 7C

IMPLANTABLE DUAL RESERVOIR ACCESS PORT

CROSS REFERENCE TO RELATED APPLICATIONS

This application is a divisional application of, and claims the benefit of, co-pending U.S. patent application Ser. No. 13/092,892, filed on Apr. 22, 2011, which claims priority to U.S. Provisional Patent Application No. 61/327,249, entitled "Implantable Dual Reservoir Access Port" and filed Apr. 23, 2010, the disclosures of which are incorporated herein by reference.

FIELD OF THE INVENTION

The present invention relates to implantable access ports for the infusion of fluids into a patient and/or withdrawal of fluids from the patient and, more specifically, to dual reservoir vascular access ports.

BACKGROUND OF THE INVENTION

Implantable vascular access ports are used extensively in the medical field to facilitate the performance of recurrent therapeutic tasks. A typical access port comprises a needle-impenetrable housing having a fluid reservoir that is sealed by a needle penetrable septum. The access port also includes an outlet stem which projects from the housing and provides a fluid passageway that communicates with the fluid reservoir. The outlet stem is used to couple the housing to a catheter. Specifically, the vascular access port is attached to the proximal end of the catheter. The distal end of the catheter is placed into a vessel. The access port is generally implanted subcutaneously at a location that is easily accessible.

Once the vascular access system is implanted, a non-coring needle, e.g., a Huber needle, attached to a feed line may be used to access the implanted vascular access port, by penetrating the septum, to deliver a desired medication. Alternatively, bodily fluids can be withdrawn from the location where the distal end of the catheter is placed.

Many conventional access ports in use contain a single fluid reservoir through which medication can be delivered to a patient. Such structures can, however, be severely limiting to medical practitioners. For example, it is often desirable to deliver medications that are incompatible when mixed together in a single fluid reservoir prior to infusion into the body of the patient. Alternatively, it may be desirable to use one lumen to deliver medication to a patient and use a second lumen to withdraw blood samples for testing. In fact, some medical institutions have policies that require that one lumen of an implantable port is dedicated for infusion and the other is dedicated solely for the withdrawal of blood samples. Such plural functions cannot be performed through the use of a single reservoir access port.

Conventional dual reservoir access ports have been developed. A conventional dual reservoir access port typically comprises a port base having a pair of separate reservoirs formed therein: a medial fluid reservoir and a lateral fluid reservoir. Each of the fluid reservoirs has a corresponding access opening that is sealed by an individual septum. The individual septa are secured in place by a cap that engages the port base. In some other designs, a single septum (e.g., compound septum) can be used to seal both reservoirs.

An outlet stem housing a pair of fluid passageways projects from the exterior of the port base, which outlet stem may be between the pair of fluid reservoirs, or at the distal end of the access port and in-line with the two fluid reservoirs. When the outlet stem is placed between the fluid reservoirs, the fluid reservoirs are arranged side-by-side, and the outlet stem projects from a longitudinal side of the housing. This placement of the outlet stem causes the fluid reservoirs to be spaced relatively far apart, increasing the overall size of the access port.

During the implantation procedure for a conventional implantable access port having a single reservoir, a subcutaneous pocket is first created to receive and house the access port. This is done by making an incision in the skin of the patient at the intended implantation site for the access port. The access port is then inserted beneath the skin through the incision. The outlet stem of the access port is usually received within the pocket last, after the proximal end of the access port is placed in the subcutaneous pocket. A catheter is then coupled to the outlet stem of the access port.

To implant a conventional side-by-side access port, an incision must be made at the implantation site that is at least as long as the access port. Only in this way can the access port be received through the incision followed by the outlet stem. The longer the incision, the longer the healing process before the access port can be freely utilized and the greater the potential for infection or other complications.

SUMMARY OF THE INVENTION

In accordance with an aspect of the present invention there is provided an access port base comprising a proximal end, a distal end, a proximal fluid reservoir, a distal fluid reservoir, a dual prong outlet stem projecting from the distal end of the access port base, a first fluid channel, a second fluid channel, and a puncture shield. The proximal fluid reservoir comprises a bottom wall at a bottom of the proximal fluid reservoir and is disposed at the proximal end of the access port base. The distal fluid reservoir comprises a bottom wall at a bottom of the distal fluid reservoir and is disposed at the distal end of the access port base. The dual prong outlet stem comprises a first prong comprising a first distal tip, and a second prong comprising a second distal tip. The first fluid channel extends through the first prong and a first portion of the access port base and provides a first fluid pathway from the first distal tip of the first prong to the distal fluid reservoir. The second fluid channel extends through the second prong and a second portion of the access port base and provides a second fluid pathway from the second distal tip of the second prong to the proximal fluid reservoir. A first portion of the second fluid channel is disposed in the bottom wall of the distal fluid reservoir beneath the distal fluid reservoir. At least a portion of the puncture shield is disposed in the bottom wall of the distal fluid reservoir between the distal fluid reservoir and the second fluid pathway.

In accordance with another aspect of the present invention there is provided an access port comprising a base, a first needle-penetrable septum disposed atop a distal fluid reservoir of the base, a second needle-penetrable septum disposed atop a proximal fluid reservoir of the base, and a cap securing the first and second needle-penetrable septa to the base. The base comprises a proximal end, a distal end, the proximal fluid reservoir, the distal fluid reservoir, a dual prong outlet stem, a first fluid channel, a second fluid channel, and a puncture shield. The proximal fluid reservoir comprises a bottom wall at a bottom of the proximal fluid reservoir and is disposed at the proximal end of the base. The distal fluid reservoir comprises a bottom wall at a bottom of the distal fluid reservoir and is disposed at the distal end of the base. The dual prong outlet stem projects from the distal end of the base and comprises a first prong comprising a first distal tip, and a second prong comprising a second distal tip. The first fluid channel extends through the first prong and a first portion of the base and provides a first fluid pathway from the first distal tip of the first prong to the distal fluid reservoir. The second fluid channel extends through the second prong and a second portion of the base and provides a second fluid pathway from the second distal tip of the second prong to the proximal fluid reservoir. A first portion of the second fluid channel is disposed in the bottom wall of the distal fluid reservoir beneath the distal fluid reservoir. At least a portion of the puncture shield is disposed in the bottom wall of the distal fluid reservoir between the distal fluid reservoir and the second fluid pathway. The cap secures the first and second needle-penetrable septa to the base to form a fluid seal between the first septum and the distal fluid reservoir and between the second septum and the proximal fluid reservoir. The cap comprises a distal opening corresponding to the first needle-penetrable septum and the distal fluid reservoir, a proximal opening corresponding to the second needle-penetrable septum and the proximal fluid reservoir, and a lower skirt portion.

In accordance with yet another aspect of the present invention there is provided an access port comprising a base, a first needle-penetrable septum disposed atop a distal fluid reservoir of the base, a second needle-penetrable septum disposed atop a proximal fluid reservoir of the base, and a cap securing the first and second needle-penetrable septa to the base. The base comprises a proximal end, a distal end, the proximal fluid reservoir, the distal fluid reservoir, a dual prong outlet stem, a first fluid channel, a second fluid channel, and means for preventing puncture of the second fluid channel. The proximal fluid reservoir comprises a bottom wall at a bottom of the proximal fluid reservoir and is disposed at the proximal end of the base. The distal fluid reservoir comprises a bottom wall at a bottom of the distal fluid reservoir and is disposed at the distal end of the base. The dual prong outlet stem projects from the distal end of the base and comprises a first prong comprising a first distal tip, and a second prong comprising a second distal tip. The first fluid channel extends through the first prong and a first portion of the base and provides a first fluid pathway from the first distal tip of the first prong to the distal fluid reservoir. The second fluid channel extends through the second prong and a second portion of the base and provides a second fluid pathway from the second distal tip of the second prong to the proximal fluid reservoir. A first portion of the second fluid channel is disposed in the bottom wall of the distal fluid reservoir beneath the distal fluid reservoir. The cap secures the first and second needle-penetrable septa to the base to form a fluid seal between the first septum and the distal fluid reservoir and between the second septum and the proximal fluid reservoir. The cap comprises a distal opening corresponding to the first needle-penetrable septum and the distal fluid reservoir, a proximal opening corresponding to the second needle-penetrable septum and the proximal fluid reservoir, and a lower skirt portion.

BRIEF DESCRIPTION OF THE DRAWINGS

For the purpose of illustration, there are shown in the drawings certain embodiments of the present invention. In the drawings, like numerals indicate like elements throughout. It should be understood, however, that the invention is not limited to the precise arrangements, dimensions, and instruments shown. In the drawings:

FIG. 2 is a perspective view of the embodiment of the dual reservoir access port of FIG. 1 in which the dual reservoir access port is assembled and attached to the dual lumen catheter via the locking collar, in accordance with an exemplary embodiment of the present invention;

FIG. 3 is a cross-sectional view of the embodiment of the dual reservoir access port of FIG. 1 taken along a section line A-A illustrated in FIG. 2, in accordance with an exemplary embodiment of the present invention;

FIG. 6 is an elevation view of a dual prong outlet stem of the embodiment of the dual reservoir access port of FIG. 1, in accordance with an exemplary embodiment of the present invention;

FIG. 7A is another elevation view of the dual prong outlet stem of the dual reservoir access port of FIG. 1 from a line G-G shown in FIG. 6, in accordance with an exemplary embodiment of the present invention;

FIG. 7B is a cross-sectional view of the dual prong outlet stem of FIG. 6 taken along a section line H-H, in accordance with an exemplary embodiment of the present invention;

FIG. 7C is a cross-sectional view of the dual prong outlet stem of FIG. 6 taken along a section line I-I illustrated in FIG. 7A, in accordance with an exemplary embodiment of the present invention;

FIG. 8 is a cross-sectional view of the dual lumen catheter of FIG. 1 taken along a section line B-B illustrated in FIG. 2, in accordance with an exemplary embodiment of the present invention;

DETAILED DESCRIPTION OF THE INVENTION

The words "proximal" and "distal" refer to directions away from and closer to, respectively, a physician implanting the access port assembly. Specifically to this invention, the distal end of the exemplary dual reservoir access port refers to the end of the access port that connects to a catheter, and the proximal end of the catheter refers to the end of the catheter that connects to the access port assembly.

A dual reservoir access port (also referred to herein as a "dual reservoir port," "access port," or "implantable port") with an outlet stem arranged in-line with its two fluid reservoirs has a distinct advantage in that the incision required for implantation is only as wide as the width of the access port, and not the length of the access port. In addition, the in-line port design also provides improved cosmetics and aesthetics.\

Compared to a conventional side-by-side dual reservoir access port, the in-line configuration of the dual reservoirs leads to difficulties in arranging internal fluid passageways. Particularly, because the distal reservoir in an in-line dual reservoir access port is located between the proximal reservoir and the outlet stem, internal fluid passageways must be carefully designed to connect the proximal reservoir to the outlet stem.

A conventional in-line dual reservoir access port generally employs an internal fluid passageway that goes around the distal reservoir. Such fluid passageway around the distal reservoir is usually small and tortuous, which poses difficulties for certain medical procedures.

Figure 1:
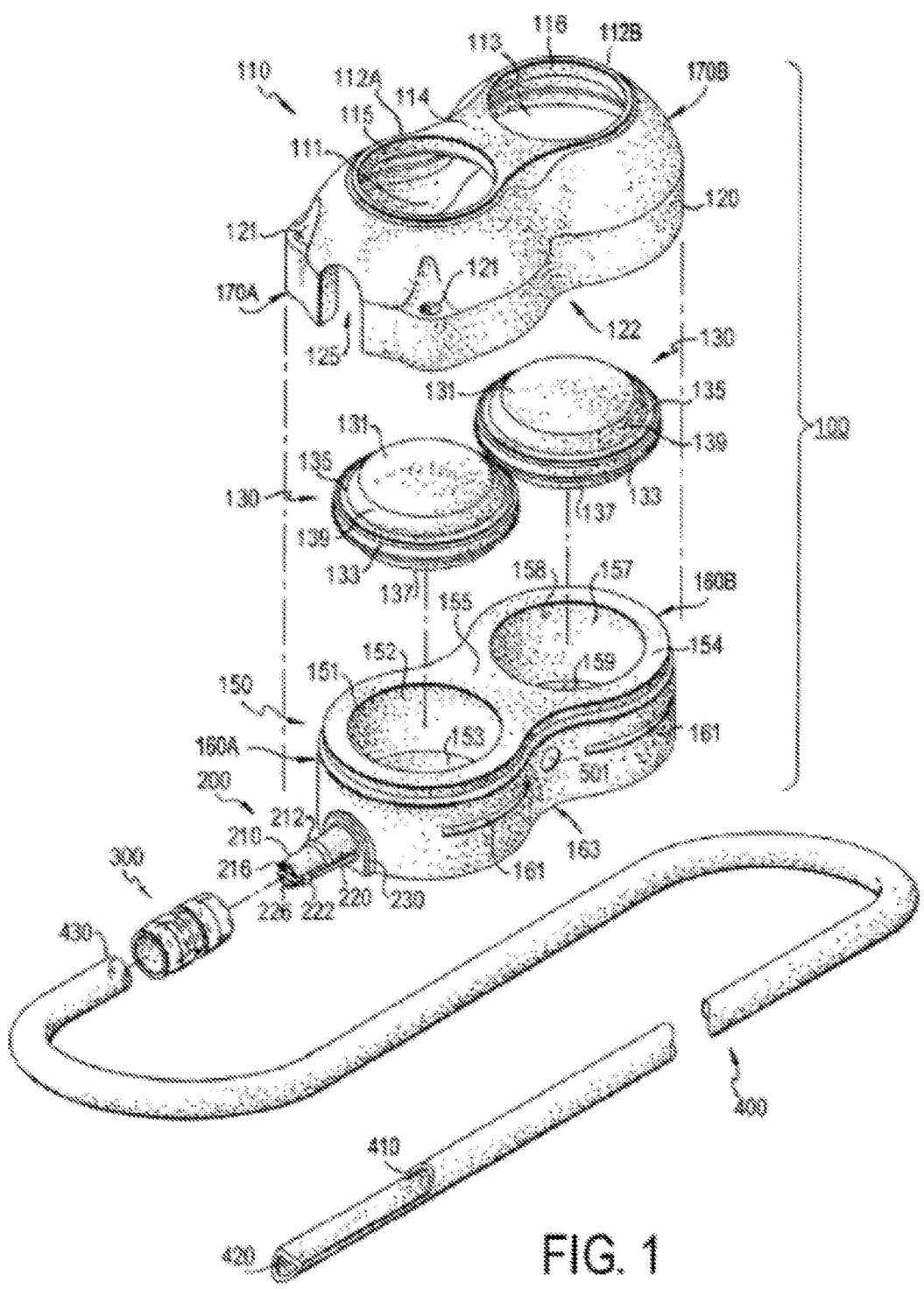
FIG. 1 is an exploded view of an exemplary embodiment of a dual reservoir access port assembly comprising a dual reservoir access port, a dual lumen catheter, and a locking collar, in accordance with an exemplary embodiment of the present invention.

Illustrated in FIG. 1 is an exploded view of the elements of an exemplary embodiment of a dual reservoir access port assembly, in accordance with an exemplary embodiment of the present invention. The dual reservoir access port assembly comprises a dual reservoir port 100, a dual prong outlet stem 200, a locking collar 300, and a dual lumen catheter 400. The dual reservoir port 100 further comprises a cap 110, two individual needle penetrable septa 130, and a port base 150.

The port base 150 comprises a distal fluid reservoir 151 located at a distal end 160A of the port base 150 and a proximal fluid reservoir 157 located at a proximal end 160B of the port base 150. The distal reservoir 151 and the proximal reservoir 157 are generally of cylindrical shape, each having a generally flat bottom wall 153 159, respectively, and a sidewall 152 158, respectively. Alternatively, the reservoirs may be of any other shape, such as generally D-shaped, C-shaped, stadium shaped, oval, triangular, rectangular, or trapezoidal. Additionally, the distal and proximal reservoirs 151 157 may be of different shapes. In the embodiment illustrated in FIG. 1, the distal reservoir 151, the proximal reservoir 157, and the dual prong outlet stem 200 are arranged in-line with each other. The distal reservoir 151 and the proximal reservoir 157 are separated by a dividing wall 155. Preferably, the length of the dividing wall 155 is narrower than the maximum width of the distal reservoir 151 and the proximal reservoir 157, thereby creating a narrowed midsection 163 in the port base 150.

The needle penetrable septa 130 are placed atop each of the distal reservoir 151 and the proximal reservoir 157. In the particular embodiment shown, each of the individual septa 130 comprises an upper dome 131, an upper compression zone 139, a flange 133, and a lower plug 137. The upper dome 131 provides tactile feedback to a medical practitioner as to the center of the individual septum 130. The flange 133 comprises a ring of thin material that is disposed around the circumference of each of the septa 130. The flange 133 further comprises a top surface 135 and a bottom surface 136 (illustrated in FIG. 10A). The bottom surface 136 of the flange 133 of each septa 130 is placed on an upper surface 154 of the port base 150. The lower plug 137 of the flange 133 extends into a portion of the respective distal or proximal reservoirs 151 157. The outer diameter of the lower plug 137 is preferably sized to be slightly larger than the inner diameter of the distal and proximal reservoirs 151 157, so that when placed in the reservoirs, radial compression is achieved against the lower plug 137 of each of the septa 130.

The cap 110 is of a generally elongated domed shape and comprises a distal opening 111 at a distal end 170A of the cap 110, a proximal opening 113 located at a proximal end 170B of the cap 110, and a skirt 120. The distal opening 111 and the proximal opening 113 are generally circular in shape, and receive the upper domes 131 of the septa 130 for the distal and proximal reservoirs 151 157, respectively. The shape of the distal and proximal openings 111 113 may also conform to any alternative shape of the distal and proximal reservoirs 151 157. The distal opening 111 and the proximal opening 113 are also each encircled by a respective generally flat top rim 112A 112B. The rims are separated by a divider 114. The distal opening 111 and the proximal opening 113 also each have an interior sidewall 115 116, respectively. In the embodiment shown, the sidewalls 115 116 are angled, i.e., the sidewalls 115 116 are of a generally truncated cone shape, encircling a narrower top opening and a wider bottom opening. The interior side walls 115 116 contact a top portion of the upper compression zone 139 of the individual septa 130.

The cap 110 is placed over the individual septa 130 and the port base 150, engaging the port base 150 through a locking mechanism to secure the septa 130 to the port base 150. In this particular embodiment, a number of receiving grooves 161 are disposed on the exterior side wall of the port base 150. The receiving grooves 161 engage locking ribs 162 (illustrated in FIGS. 4A and 4B) disposed on the corresponding interior wall of the cap 110. When the cap 110 is locked to the port base 150, the cap 110 compresses the septa 130 against the port base 150, creating a fluid seal between the distal septum 130 and both the distal reservoir 151 and the cap 110 and a fluid seal between a proximal septum 130 and both the proximal reservoir 157 and the cap 110. In an exemplary embodiment, the cap 110 may be solvent bonded to the port base 150.

The skirt 120 generally follows the outer contour of the port base 150. The skirt 120 preferably also has a narrowed midsection 122 at roughly the middle point of the implantable port 100 corresponding to the narrowed midsection 163 in the port base 150. The narrowed midsection 122 of the skirt 120 provides a medical practitioner tactile feedback as to the center of the implantable port 100, thereby facilitating identification of the distal reservoir 151 and the proximal reservoir 157. The skirt 120 preferably includes a plurality of suture holes 121 for suturing the implantable port 100 to the surrounding tissue when implanted in a patient.

The dual prong outlet stem 200 is attached to the distal end 160A of the port base 150. The dual prong outlet stem 200 comprises an upper prong 210 and a lower prong 220. The upper prong 210 and the lower prong 220 have a proximal base 230 that connects to the port base 150. The lower skirt portion 120 preferably includes an opening 125 for receiving the proximal stem base 230 of the dual prong outlet stem 200. The upper prong 210 and the lower prong 220 have a generally semicircular (D-shaped) cross section, and a slight taper toward their respective distal tips 216 and 226. The distal tips 216 and 226 form the distal tip of the dual prong outlet stem 200. In an exemplary embodiment, the dual prong outlet stem 200 is formed integrally with the base 150. In another exemplary embodiment, the dual prong outlet stem 200 is formed separately from the base 150 and solvent bonded to the base 150.

The dual prong outlet stem 200 is designed to receive the dual lumen catheter 400. The dual lumen catheter 400 has a proximal end 430 that connects to the dual prong outlet stem 200. Each of the lumens of the dual lumen catheter has an opening at the distal tips 410 420 of the lumens of the catheter 400. The proximal end 430 of the catheter lumens is designed to fit over the upper and lower prongs 210 220 of the dual prong outlet stem 200.

Each lumen of the dual lumen catheter 400 has a distal opening at respective distal tips 410 420. In the embodiment shown in FIG. 1, the distal openings 410 420 are staggered. In this particular example, the distal tips 410 420 are produced by skiving, i.e., using a sharp instrument to remove a portion of the exterior wall of one lumen of the dual lumen catheter 400 along the dividing wall, thereby creating staggered distal openings at the distal tips 410 420. Other catheter tip configurations, e.g., blunt tip, split tip, etc., and manufacturing techniques, such as cutting, welding, attaching, etc., can be adapted to produce the distal catheter tips 410 420 of the dual lumen catheter 400.

Depicted in FIG. 2 is a perspective view of the dual reservoir port 100 assembled and attached to the dual lumen catheter 400 using the locking collar 300, in accordance with an exemplary embodiment of the present invention. During assembly, each of the septa 130 are placed onto the respective reservoirs 151 157, and the cap 110 is placed over the septa 130 and locked onto the port base 150, thereby compressing and securing the individual septa 130 between the port base 150 and the cap 110. The upper domes 131 of the individual septa 130 protrude from the distal opening 111 and the proximal opening 113 of the cap 110. The lower plugs 137 of the individual septa 130 protrude into a portion of the reservoirs 151 157.

When connecting the dual lumen catheter 400 to the assembled dual reservoir port 100, the proximal end 430 of the dual lumen catheter 400 is slipped onto the dual prong outlet stem 200, with the upper prong 210 placed in one lumen, and the lower prong 220 placed in the other lumen of the catheter 400. The locking collar 300 is slipped over the proximal end 430 of the dual lumen catheter 400 toward the dual prong outlet stem 200, thereby securing the dual lumen catheter 400 on the dual prong outlet stem 200.

FIG. 3 illustrates an exemplary cross-sectional view of the dual reservoir port 100 taken along a section line A-A illustrated in FIG. 2, in accordance with an exemplary embodiment. As can be seen in FIG. 3, the cap 110 is snapped onto the port base 150 securing the individual septa 130. The upper domes 131 of the septa 130 protrude from their respective distal opening 111 and proximal opening 113 of the cap 110. FIG. 3 also illustrates that, for this particular embodiment, the dual prong outlet stem 200 is constructed as one piece with the port base 150, i.e., it is integrally formed with the port base 150.

Referring to FIGS. 1 and 3 together, there are illustrated the upper prong 210 and lower prong 220 of the dual prong stem 200, in accordance with an exemplary embodiment of the present invention. An upper fluid channel 171 extends through the upper prong 210 and a portion 164A (illustrated in FIG. 5A) of the port base 150 to provide a first, upper fluid passageway or pathway 173 (illustrated in FIG. 5A) for fluid communication between the distal opening in the distal tip 216 of the upper prong 210 and the distal reservoir 151. The upper fluid channel 171 opens to the distal reservoir 151 at a proximal opening 218 in a lower portion of the side wall 152 of the distal reservoir 151 close to the bottom 153 of the distal reservoir 151.

A lower fluid channel 172 extends through the lower prong 220 and a portion 164B (illustrated in FIGS. 5B-5C) of the port base 150 to provide a second, lower fluid passageway or pathway 174 (illustrated in FIGS. 5B-5C) for fluid communication between the distal opening in the distal tip 226 of the lower prong 220 and the proximal reservoir 157. The lower fluid channel 172 opens to the proximal reservoir 157 at a proximal opening 228 in a lower portion of the side wall 158 of the proximal reservoir 157 and close to the bottom 159 of the proximal reservoir 157.

The upper prong 210 and the lower prong 220 and the upper fluid channel 171 and the lower fluid channel 172 are stacked vertically, i.e., one is disposed above the other, in the exemplary embodiments shown in FIGS. 1 and 3. Alternatively, the prongs of the dual prong outlet stem 200 may be arranged horizontally, or with a horizontal or vertical offset with respect to each other. The portion 164B of the lower fluid channel 172 is located beneath the distal reservoir 151. The material thickness between the bottom 153 of the distal reservoir 151 and the top of the lower fluid channel 172 is rather thin. Without the precautions described below, there is a perceived risk that a needle entering into the distal reservoir 151 may puncture through and enter the lower fluid channel 172, compromising the fluid separation of the distal and proximal reservoirs 151 157.

Figure 4A:
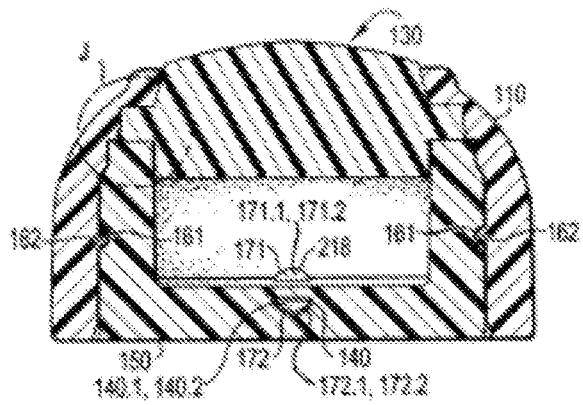
FIG. 4A is a cross-sectional view of the embodiment of the dual reservoir access port of FIG. 1 taken along a section line C-C illustrated in FIG. 3, in accordance with an exemplary embodiment of the present invention.
Figure 4B:
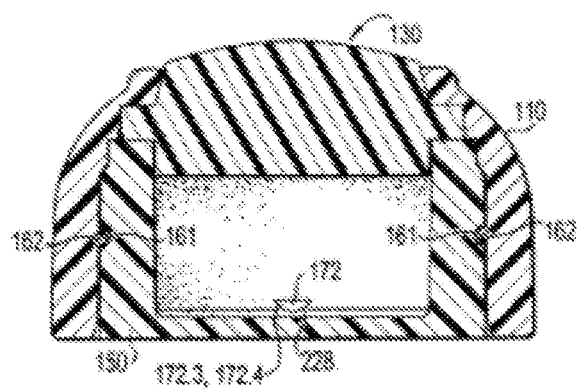
FIG. 4B is a cross-sectional view of the embodiment of the dual reservoir access port of FIG. 1 taken along a section line D-D illustrated in FIG. 3, in accordance with an exemplary embodiment of the present invention.
Figure 5A:
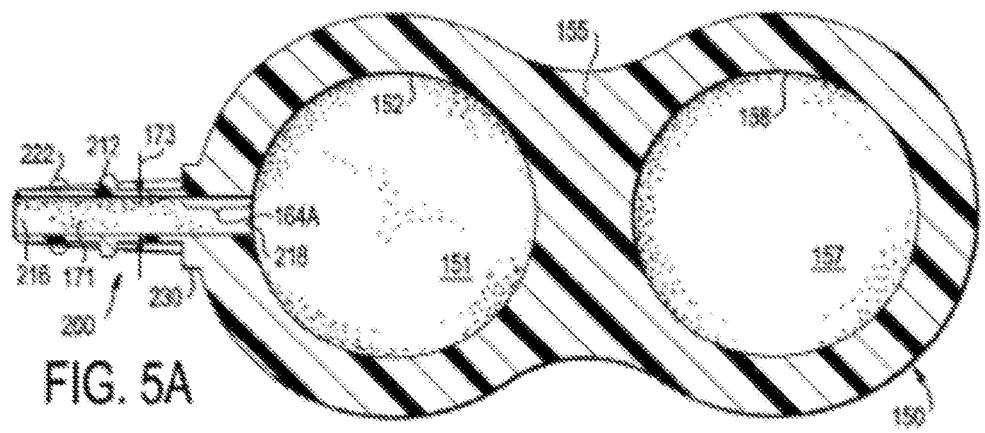
FIG. 5A is a cross-sectional view of the embodiment of the dual reservoir access port of FIG. 1 taken along a section line E-E illustrated in FIG. 3, in accordance with an exemplary embodiment of the present invention.
Figure 5B:
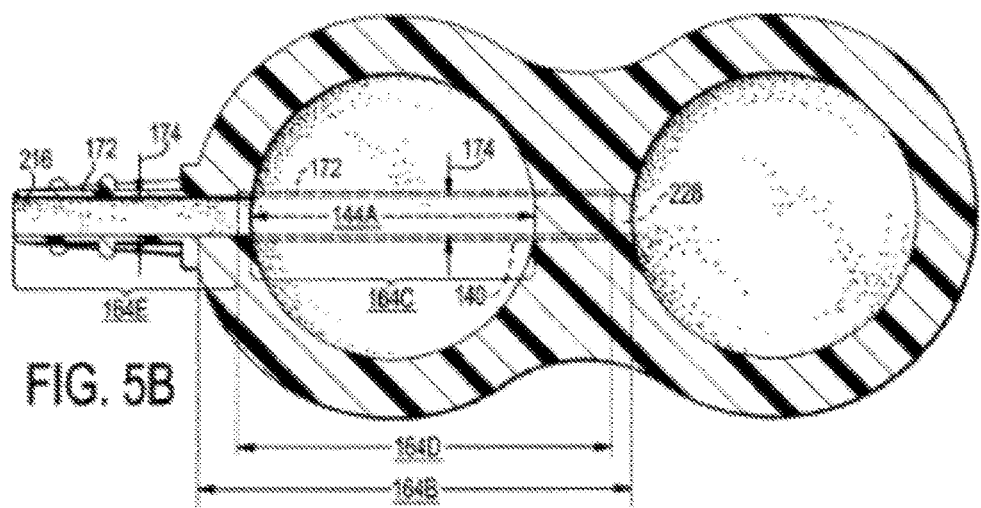
FIG. 5B is a cross-sectional view of the embodiment of the dual reservoir access port of FIG. 5A, additionally showing a puncture shield and a fluid pathway in dashed lines, in accordance with an exemplary embodiment of the present invention.
Figure 5C:
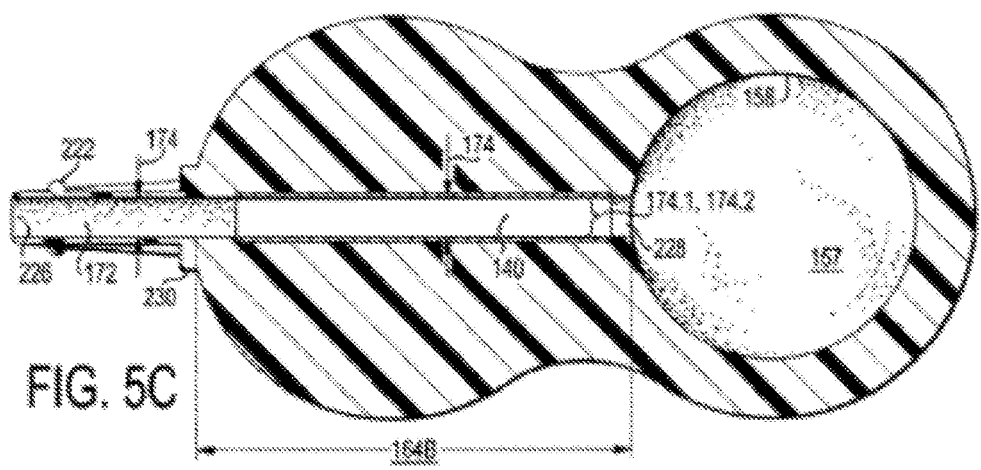
FIG. 5C is a cross-sectional view of the embodiment of the dual reservoir access port of FIG. 1 taken along a section line F-F illustrated in FIG. 3, in accordance with an exemplary embodiment of the present invention.

FIG. 4A is a cross-sectional view of the embodiment of the dual reservoir access port of FIG. 1 taken along a section line C-C illustrated in FIG. 3, in accordance with an exemplary embodiment of the present invention. FIG. 4B is a cross-sectional view of the embodiment of the dual reservoir access port of FIG. 1 taken along a section line D-D illustrated in FIG. 3, in accordance with an exemplary embodiment of the present invention. FIG. 5A is a cross-sectional view of the embodiment of the dual reservoir access port of FIG. 1 taken along a section line E-E illustrated in FIG. 3, in accordance with an exemplary embodiment of the present invention. FIG. 5B is a cross-sectional view of the embodiment of the dual reservoir access port of FIG. 5A, additionally showing a puncture shield and a fluid pathway in dashed lines, in accordance with an exemplary embodiment of the present invention. FIG. 5C is a cross-sectional view of the embodiment of the dual reservoir access port of FIG. 1 taken along a section line F-F illustrated in FIG. 3, in accordance with an exemplary embodiment of the present invention.

A cross section of the upper fluid channel 171 is visible in FIG. 4A. As illustrated in FIG. 4A, the upper fluid channel 171 comprises a lumen 171.1 which is of a generally semicircular cross section 171.2, i.e., it has a semicircular or D-shaped lumen 171.1, throughout the length of the upper fluid channel 171. Because the upper fluid channel 171 forms the first, upper fluid pathway 173, the fluid pathway 173 also comprises the lumen 171.1 with the generally semicircular cross section 171.2 throughout the length of the fluid pathway 173.

Cross sections of the lower fluid channel 172 are illustrated in FIGS. 4A-4B. As illustrated in FIG. 4A, the lower fluid channel 172 comprises a lumen 172.1 in a portion 164D (illustrated in FIG. 5B) of the base 150. The lumen 172.1 is of a generally semicircular cross section 172.2 in the portion 164D. As illustrated in FIG. 4B, the lower fluid channel 172 further comprises a lumen 172.3 in a portion 164B of the base 150 between the portion 164D and the proximal fluid reservoir 157. The lumen 172.3 is of a generally semicircular cross section 172.4 in this portion. It is to be understood that the lower fluid channel 172 in this portion is the same as in a portion 164E of the base 150E outside the portion 164D between the portion 164D and the distal tip 226. Thus, the lower fluid channel 172 comprises the lumen 172.3 in the portion 164E having a semi-circular cross section 172.4.

Referring to FIGS. 3, 4A, and 5B-5C together, there is illustrated an exemplary puncture shield 140, in accordance with an exemplary embodiment of the present invention. FIG. 4A illustrates an exemplary cross-sectional view of the puncture shield 140 taken along the section line C-C shown in FIG. 3. As illustrated in FIG. 4A, the puncture shield 140 comprises a lumen 140.1 which is of a generally semicircular cross section 140.2, i.e., it has a semicircular or D-shaped lumen 140.1, throughout the length of the puncture shield 140. FIGS. 5A-5B illustrate exemplary cross-sectional views of the dual reservoir access port 100 of FIG. 1.

As seen in these figures, at least a portion 144A of the puncture shield 140 is disposed within the portion 164C of the lower fluid channel 172 directly underneath the bottom 153 of the distal reservoir 151 to protect against potential needle penetration into the lower fluid channel 172. The puncture shield 140 is also disposed between the bottom 153 of the distal fluid reservoir 151 and the second fluid pathway 174. It is to be understood that the puncture shield 140 may extend through the lower fluid channel 172 beyond the walls 152 of the distal fluid reservoir 151, such as through the portion 164D illustrated in FIGS. 5B-5C. In an exemplary embodiment, the puncture shield 140 is a metal or metal alloy tube lining at least the portion 164C of the lower fluid channel 172 directly underneath the distal reservoir 151.

It is to be understood that the upper and lower fluid channels 171 172 may also have alternatively shaped lumens 171.1, 172.1, and 172.3, such as circular, oval, C-shaped, oval, elliptical, or stadium-shaped (rectangular with semi-circular ends) cross sections. It is also to be understood that the puncture shield 140 can be of other sizes and shapes, such as C-shaped, stadium shaped, oval, triangular, rectangular, or trapezoidal, to match the lumens 171.1, 172.1, and 172.3 if they are C-shaped, stadium shaped, oval, triangular, rectangular, or trapezoidal.

Figure 4C:
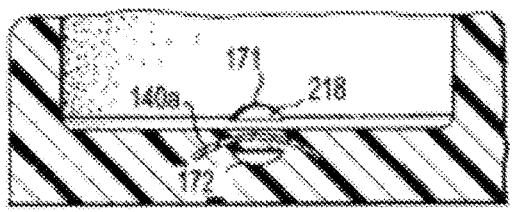
FIGS. 4C-4G illustrate exemplary cross-sectional views of further embodiments of the dual reservoir access port of FIG. 1 taken along the section line C-C illustrated in FIG. 3, in accordance with an exemplary embodiment of the present invention.

Still other configurations of the puncture shield 140 are contemplated. Referring now to FIG. 4C, there is illustrated a view of a cross section of another exemplary puncture shield, generally designated as 140a, in accordance with an exemplary embodiment of the present invention. The cross-section is taken along section line C-C shown in FIG. 3. The puncture shield 140a is disposed in the port base 150 between the bottom 153 of the distal reservoir 151 and the lower fluid channel 172 to protect against needle penetration into the lower fluid channel 172. The puncture shield 140a comprises a curved strip of material that covers the top of the lower fluid channel 172 for at least the portion 164C that is underneath the bottom 153 of the distal reservoir 151.

Figure 4D:

Referring now to FIG. 4D, there is illustrated a view of a cross section of another exemplary puncture shield, generally designated as 140b, in accordance with an exemplary embodiment of the present invention. The cross-section is taken along the line C-C shown in FIG. 3. The puncture shield 140b is disposed in the port base 150 between the bottom 153 of the distal reservoir 151 and the lower fluid channel 172 to protect against needle penetration into the lower fluid channel 172. The puncture shield 140b comprises a flat strip of material that covers the top of the lower fluid channel 172 for at least the portion 164C that is underneath the bottom 153 of the distal reservoir 151.

Figure 4E:

Referring now to FIG. 4E, there is illustrated a view of a cross section of another exemplary puncture shield, generally designated as 140c, in accordance with an exemplary embodiment of the present invention. The cross-section is taken along line C-C shown in FIG. 3. The puncture shield 140c is disposed in the port base 150 underneath the bottom 153 of the distal reservoir 151 to protect against needle penetration into the lower fluid channel 172. The puncture shield 140c comprises a tube of material that surrounds the lower fluid channel 172 for at least the portion 164C that is underneath the bottom 153 of the distal reservoir 151.

Figure 4F:

Referring now to FIG. 4F, there is illustrated a view of a cross section of another exemplary puncture shield, generally designated as 140d, in accordance with an exemplary embodiment of the present invention. The cross-section is taken along the line C-C shown in FIG. 3. The puncture shield 140d is disposed at the bottom 153 of the distal reservoir 151 to protect against needle penetration into the lower fluid channel 172. Specifically, the puncture shield 140d is a material that lines the bottom 153 of the distal reservoir 151. In an exemplary embodiment, the puncture shield 140d is generally circular.

Figure 4G:

Referring now to FIG. 4G there is illustrated a view of a cross section of another exemplary puncture shield, generally designated as 140e, in accordance with an exemplary embodiment of the present invention. The cross-section is taken along line C-C shown in FIG. 3. The puncture shield 140c is disposed in the port base 150 underneath the bottom 153 of the distal reservoir 151 to protect against needle penetration into the lower fluid channel 172. The puncture shield 140e comprises a disk of material that covers the top of the lower fluid channel 172 for at least the portion 164C that is underneath the bottom 153 of the distal reservoir 151.

In the embodiments of the puncture shields shown in FIGS. 3, 4A, and 4C-4G, the puncture shields are formed from a material that is harder than the material forming the port base 150. More preferably, the material is one that, at a thin thickness, would withstand penetration by a infusion needle. In an exemplary embodiment, titanium is used for the construction of the puncture shield 140 and 140a-e. In the examples shown, the titanium puncture shield has a thickness of approximately 0.005 inches. Other metals or metal alloys, e.g., stainless steel, may also be suitable for constructing the puncture shield. The puncture shields shown in FIGS. 3, 4A, and 4C-4G are for preventing penetration into the lower fluid channel 172 by an infusion needle accessing the distal reservoir 151.

The use of a puncture shield allows a minimal distance between the bottom 153 of the distal reservoir 151 and the top of the lower fluid channel 172, which translates to an overall low profile of the dual reservoir access port 100 according to an exemplary embodiment of the present invention. In the embodiment shown in FIGS. 3 and 4A, this distance is approximately 0.020 inches. The resulting dual reservoir access port 100 has an overall height similar to a single reservoir low profile access port.

Referring again to FIG. 4A, there is also illustrated the arrangement of the cap 110, the port base 150, and the individual septum 130. The cap 110 is snapped on the port base 150, compressing the individual septum 130 to effect a fluid seal. Receiving grooves 161 along the exterior wall of the port base 150 engage locking ribs 162 on the corresponding interior surface of the cap 110 providing a locking mechanism in this embodiment. FIG. 4B also illustrates the receiving grooves 161 along the exterior wall of the port base 150, which grooves 161 engage the locking ribs 162 on the corresponding interior surface of the cap 110 to provide the locking mechanism.

FIG. 5A illustrates an exemplary view of a cross section of the dual reservoir access port 100 taken along the section line E-E illustrated in FIG. 3, in accordance with an exemplary embodiment of the present invention. As illustrated in FIG. 5A, the upper fluid channel 171 extends from the distal tip 216 of the upper prong 210 of the stem 200 through the portion 164A of the base 150 and to the distal reservoir 151. The upper fluid channel 171 opens to the distal reservoir 151 via the opening 218 in the distal side of the sidewall 152 of the reservoir 151. As shown in FIG. 5A, the upper fluid channel 171 provides a first, upper fluid pathway 173 from the distal tip 216 of the upper prong 210 of the stem 200 through the portion 164A of the base 150 and to the distal reservoir 151.

FIG. 5B illustrates an exemplary view of a cross section of the dual reservoir access port 100 also taken along the section line E-E illustrated in FIG. 3, in accordance with an exemplary embodiment of the present invention. The view in FIG. 5B differs from that in FIG. 5A because of the illustration of the lower fluid channel 172 and the puncture shield 140 in FIG. 5B in dashed lines. The lower fluid channel 172 and the puncture shield 140 are shown in dashed lines to indicate that they lie below the bottom 153 of the distal fluid reservoir 151. Specifically, the portion 164C of the fluid channel 172 and the puncture shield 140 lie directly below the distal reservoir 151. The lower fluid channel 172 opens to the proximal reservoir 157 via the opening 228 in the distal side of the sidewall 158 of the reservoir 157.

FIG. 5C illustrates an exemplary view of a cross section of the dual reservoir port 100 taken along the section line F-F illustrated in FIG. 3, in accordance with an exemplary embodiment of the present invention. As illustrated in FIG. 5C, the lower fluid channel 172 extends from the distal tip of the lower prong 226 of the stem 200 through the portion 164B of the base 150 and to the distal reservoir 157. The lower fluid channel 172 opens to the proximal reservoir 157 via the opening 228 in the distal side of the sidewall 158 of the reservoir 157.

At least two embodiments for the puncture shield 140 being disposed within the lower fluid channel 172 are contemplated. In one embodiment, the portion 164D of the lower fluid channel 172 in which the puncture shield 140 is disposed is notched so that the inner lumen 140.1 of the puncture shield 140 has the same cross section 140.2 as the cross section 172.4 of the inner lumen 172.3 of the lower fluid channel 172 in the portion 164E. The fluid channel 172 outside the portion 164D and the lumen 140.1 of the puncture shield 140 together form the lower, second fluid pathway 174, which comprises a lumen 174.1 having a cross section 174.2. In this embodiment, the cross section 174.2 of the effective fluid channel 174 is the same at all points between the distal tip 226 and the opening 228.

FIGS. 5B and 5C illustrate such embodiment. As seen in the figures, the cross section 172.2 of the lumen 172.1 of the fluid channel 172 in the portion 164D is oversized to accommodate the puncture shield 140 lining the fluid channel 172 in the portion 164D. The cross section 172.4 of the lumen 172.3 of the fluid channel 172 outside the portion 164D is equal to the cross section 140.2 of the lumen 140.1 of the puncture shield 140, i.e., the cross section 174.2 of the lumen 174.1 of the fluid pathway 174 remains constant throughout its entire length.

In another embodiment, the lower fluid channel 172 contains no notch in the portion 164D. Thus, the cross section 172.2 is the same as the cross section 172.4. The cross section of the lower fluid channel 172 is constant along all lengths of the lower fluid channel 172 from the distal tip 226 to the opening 228. The puncture shield 140 is fitted in the lower fluid channel 172. Thus, the cross section 140.2 of the lumen 140.1 of the puncture shield 140 is smaller than the cross sections 172.2 and 172.4. The lumen 174.1 of the lower, second fluid pathway 174 is narrowed in the portion 164D such that the cross section 174.2 of the lower, second fluid pathway 174 is narrower in the portion 164D than the cross section 172.4.

Figure 11A:
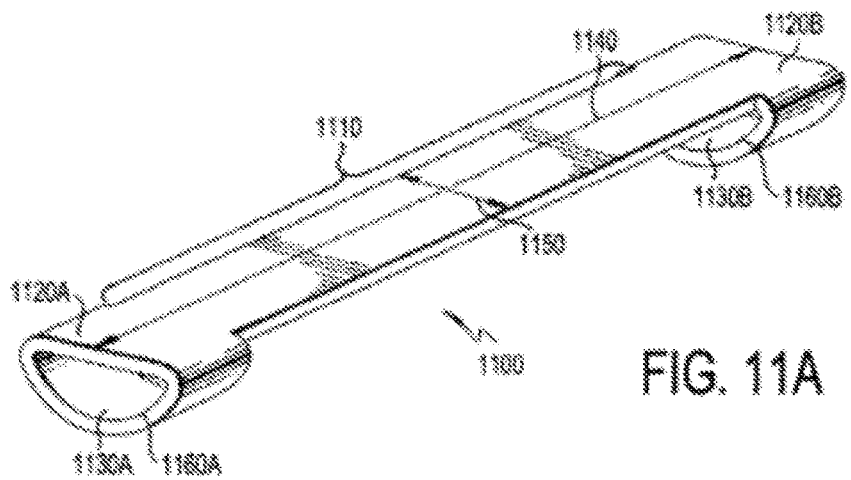
FIG. 11A illustrates an exemplary perspective view of a further embodiment of the puncture shield of FIG. 5B, in accordance with an exemplary embodiment of the present invention.
Figure 11B:
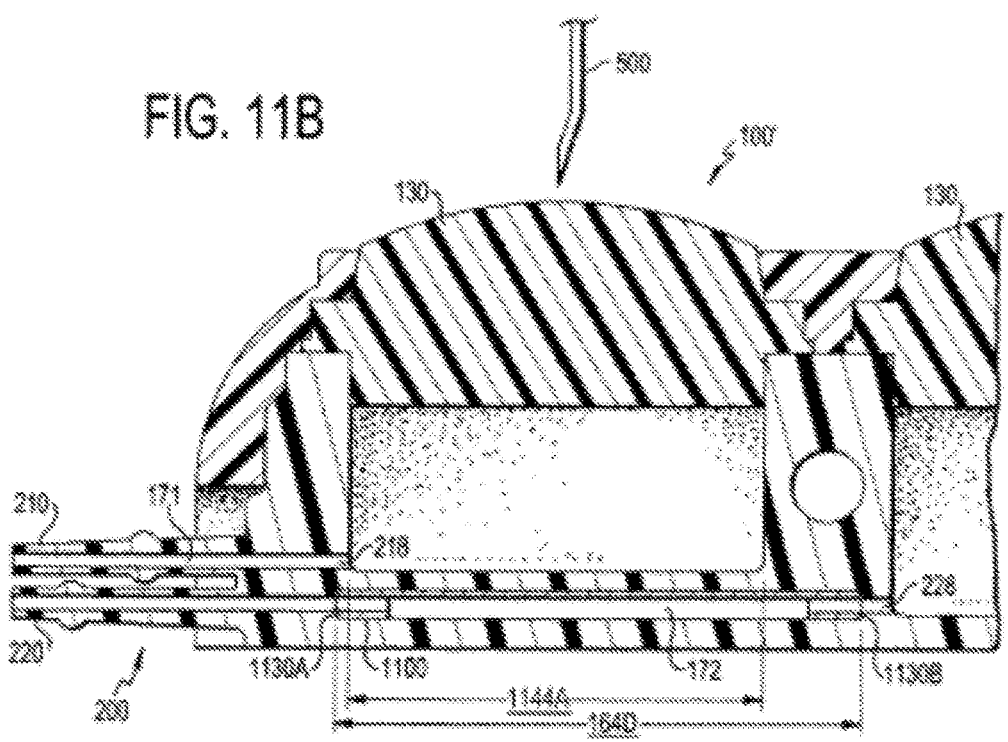
FIG. 11B illustrates an exemplary cross-sectional view of a further embodiment of the dual reservoir access port of FIG. 1, taken along a section line similar to A-A illustrated in FIG. 2, the cross-sectional view showing the puncture shield of FIG. 11A disposed within the dual reservoir access port, in accordance with an exemplary embodiment of the present invention.

When implanted in a patient, either or both of the reservoirs of the dual reservoir port 100 can be accessed from outside through a non-coring infusion needle, e.g., by a needle 500 illustrated in FIG. 11B. The infusion needle that is used to penetrate the needle penetrable individual septa 130 is typically the type referred to as a Huber needle. Because of their self-sealing nature, the individual septa 130 can withstand repeated penetration of such an infusion needle without leaking Radial compression around the circumference of the individual septa 130 facilitates the self-sealing of the septa 130.

When an infusion needle is tapped into the distal reservoir 151, fluid infused into the distal reservoir 151 travels through the upper fluid pathway 173 and into the lumen of the dual lumen catheter 400 that is connected to the upper prong 210 of the dual prong outlet stem 200. Likewise, when an infusion needle is tapped into the proximal reservoir 157, fluid infused into the proximal reservoir 157 travels through the lower fluid pathway 174 and into the lumen of the dual lumen catheter 400 that is connected to the lower prong 220 of the dual prong outlet stem 200.

The arrangement of straight fluid channels 171 172 or fluid pathways 173 174 in the dual reservoir implantable port 100 provides low resistance for fluid passing through the dual reservoir access port 100. A dual reservoir implantable port according to the present invention is particularly suitable for medical applications that may require high infusion flow rate. One particular example is power injection of contrasting agent for X-ray Computed Tomography (CT). In some applications, power injection of contrast agent is required at up to 5 ml/second flow rate. Contrast agents may also have high viscosity, which may require power injection equipment to be operated at high back pressure, and make achieving high injection flow rates challenging.

High pressure increases the risk of failure in conventional infusion systems. Rupture of an implanted port or infusion catheter, and separation of the catheter from the port may occur. Small and tortuous internal fluid passages, such as those within a conventional dual reservoir implantable port, aggravate this difficulty. The dual reservoir access port 100 of the present invention provides straight fluid channels 171 172 and fluid pathways 173 174 for both of the distal and proximal reservoirs 151 157, which fluid channels 171 172 and fluid pathways 173 174 are free from twists and turns. The fluid channels 171 172 or fluid pathways 173 174 of the dual reservoir implantable port 100 according to the present invention are also of relatively constant cross-sectional shape and size throughout. This also facilitates low resistance fluid passage through the fluid channels or pathways.

Designing a conventional dual reservoir access port to have a fluid channel disposed in a sidewall increases the width of the port, or alternatively, the height of the port. Increased width or height is not desirable as it requires increased incision size, and may lead to discomfort in patients. The dual port 100 of the present invention minimizes width as the lower fluid channel 172 is not disposed in the wall 152. It also minimizes height as the puncture shield 140 and its variations allow for a minimum distance between the bottom 153 of the distal reservoir 151 and the lower fluid channel 172. Decreased height and width allows for smaller incision size.

Further, the conventional dual reservoir access port with the fluid channel disposed in the sidewall presents other problems. Generally, an open-top fluid channel formed in the side wall around the distal reservoir is used in such designs. Such open-top channel requires a seal to prevent fluid communication with the distal reservoir. Further, such open-top fluid channel often has a large dead zone where the fluid channel width transitions to the proximal reservoir and the port stem. Such dead zones hamper proper flushing of the port. Particularly, when the proximal reservoir is used for withdrawing blood, inefficient flushing of the side wall fluid channel may result in increased risk of clot formation in the fluid channel and compromise the performance of the access port.

Referring now to FIG. 6, there is illustrated an elevation view of the outlet stem portion 200 of the dual reservoir access port 100, in accordance with an exemplary embodiment of the present invention. As can be seen in FIG. 6, the upper prong 210 has a rounded locking ridge 212 disposed around its exterior surface. The lower prong 220 also has a rounded locking ridge 222 disposed around its exterior surface. The rounded locking ridge 212 of the upper prong 210 and the rounded locking ridge 222 of the lower prong 220 are offset from each other, i.e., the rounded locking ridges 212 222 are not located at the same distance from the distal end 216 226 of the upper and lower prongs 210 220 of the dual prong outlet stem 200. In this particular example, the rounded locking ridge 212 of the upper prong 210 is located proximal, i.e., closer, to the stem base 230 compared to the rounded locking ridge 222. The rounded locking ridge 222 of the lower prong 220 is located closer to the distal end of the lower prong 220 than the locking ridge 212. The rounded locking ridge 222 is at a first distance from the distal end of the lower prong 220, and the rounded locking ridge 212 is at a second distance from the distal end of the upper prong 210 greater than the first distance. The locking ridges 212 222 have semi-circular cross sections.

FIG. 7A is another exemplary elevation view of the dual prong outlet stem portion 200 of the dual reservoir access port 100 from the line G-G illustrated in FIG. 6, in accordance with an exemplary embodiment of the present invention. FIG. 7C is an exemplary view of a cross section of the dual prong outlet stem 200 of the dual reservoir access port 100 taken along the section line I-I shown in FIG. 7A, in accordance with an exemplary embodiment of the present invention. As illustrated in FIG. 7A, each of the upper and lower prongs 210 220 of the dual prong outlet stem 200 has a generally semicircular shape.

Referring now to FIGS. 7A and 7C together, there are illustrated locking ridges of the upper and lower prongs 210 220 in further detail. Specifically, the locking ridge of the upper prong 210 includes the rounded locking ridge 212 illustrated in FIG. 6 (also referred to herein as an "exterior curved locking ridge") located on the curved outer surface of the upper prong 210 and a further locking ridge 214 (an "interior straight locking ridge") located on the flat side of the prong 210 facing the prong 220. Similarly, the locking ridge of the lower prong 220 includes the rounded locking ridge 222 illustrated in FIG. 6 (also referred to herein as an "exterior curved locking ridge") located on the curved outer surface of the lower prong 220 and a further locking ridge 224 (an "interior straight locking ridge") located on the flat side of the prong 220 facing the prong 210.

The locking ridges 212 214 for both the upper prong 210 of the dual prong outlet stem 200 and the locking ridges 222 224 of the lower prong 220 can be seen to encircle the exterior circumference of the respective prong 210 220. The exterior curved locking ridge 212 of the upper prong 210 follows the exterior curved contour of the exterior of the upper prong 210, and the interior straight locking ridge 214 of the upper prong 210 follows the generally flat side of the upper prong 210 that faces the lower prong 220. The exterior curved locking ridge 222 of the lower prong 220 follows the exterior curved contour of the exterior of the lower prong 220, and the interior straight locking 224 ridge of the lower prong 220 follows the generally flat side of the lower prong 220 that faces the upper prong 210. In this view, the locking ridges 212 214 of the upper prong 210 are offset from the locking ridges 222 224 of the lower prong 220, and are closer to the stem base 230. The curved and flat outer surfaces of the stems define the fluid channels within the prongs 210 220.

In this particular embodiment, the upper and lower prongs 210 220 are slightly tapered on their exterior curved sides and also on the flat sides that face each other. Because of the slight taper of the upper and lower prongs 210 220, the locking ridges 212 214 of the upper prong 210 are of a slightly larger circumferential length than the locking ridges 222 224 of the lower prong 220. Namely, the arc length of the locking ridge 212 is greater than the arc length of the locking ridge 222, and the length of the locking ridge 214 is greater than the length of the locking ridge 224. The upper and lower fluid channels 171 and 172 are of a generally constant size throughout their respective prongs 210 220.

Referring now to FIG. 7B, there is illustrated a view of a cross section of the dual prong outlet stem base 230 taken along the section line H-H illustrated in FIG. 6. As shown in FIG. 7B, the upper fluid channel 171 and the lower fluid channel 172 respectively comprise semicircular cross sections 171.2 and 172.2 in the base 230. In this embodiment, the upper fluid channel 171 is stacked vertically over the lower fluid channel 172.

FIG. 8 illustrates an exemplary view of a cross section of the dual lumen catheter 400 taken along the section line B-B illustrated in FIG. 2, in accordance with an exemplary embodiment of the present invention. The dual lumen catheter 400 comprises an exterior wall 480, which surrounds two lumens 440 and 450, which are separated from one another by a dividing wall 470. The exterior wall 480 of the dual lumen catheter 400 is generally of a circular or oval cross section. The lumens 440 450 are generally D-shaped or C-shaped, though other shapes may also be used. The lumens 440 450 may be of equal sizes. The interior dimensions of the lumens 440 450 are comparable to the exterior dimensions of the upper and lower prongs 210 220 of the dual prong outlet stem 200.

Figure 9A:
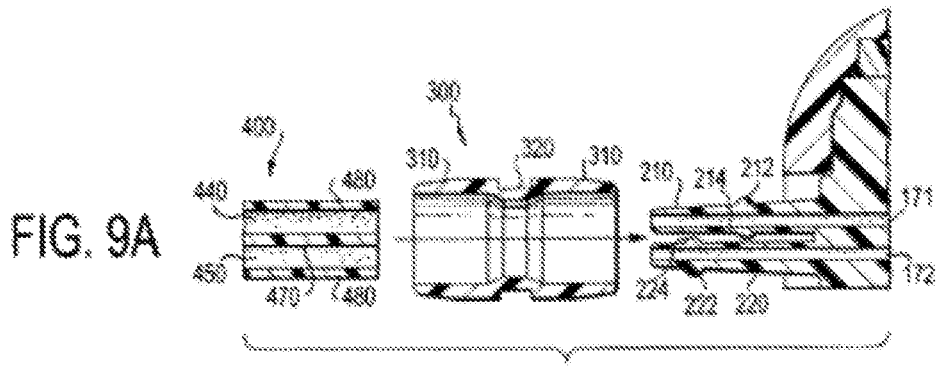
FIG. 9A is a cross-sectional side view of the dual lumen catheter and locking collar in preparation to be connected to the dual prong outlet stem of the dual reservoir access port of FIG. 1, in accordance with an exemplary embodiment of the present invention.

FIG. 9A is an exemplary cross-sectional side view of an example where a dual lumen catheter 400 and locking collar 300 are in position to be connected to the dual prong outlet stem 200 of the dual reservoir access port 100, in accordance with an exemplary embodiment of the present invention. The locking collar 300 comprises two generally hollow cylindrical shaped end sections 310 and a narrow waist 320. The two end sections 310 are identical to each other, i.e., the locking collar 300 is symmetrical about a middle point of the waist 320. The locking collar 300, therefore, can be used in either direction. The symmetrical shape greatly simplifies the connection of the dual lumen catheter 400 to the dual reservoir port 100, since a medical practitioner does not have to distinguish the orientation of the locking collar 300 during the implantation procedure.

The narrow waist 320 of the locking collar 300 has a smaller inner diameter than the end sections 310. In the embodiment shown in FIG. 9A, the interior of both of the end sections 310 gradually narrows to the inner diameter of the narrow waist 320. The inner diameter of the narrow waist 320 is slightly larger than the combined outer diameter of the upper and lower prongs 210 220 between the offset locking ridges 212 214 of the upper prong 210 and the locking ridges 222 224 of the lower prong 220. The width of the narrow waist 320 is approximately equal or slightly shorter than the offset distance between locking ridges 212 214 of the upper prong 210 and the locking ridges 222 224 of the lower prong 220.

The narrow waist 320 is designed to fit between the rounded locking ridge of the upper prong 212 and the rounded locking ridge of the lower prong 222 in its locking position, thereby frictionally securing the dual lumen catheter 400 to the dual prong outlet stem 200. When a medical practitioner connects the dual lumen catheter 400 to the dual reservoir access port 100, he first slips each lumen 440 450 of the dual lumen catheter 400 onto the upper prong 210 and lower prong 220 of the dual prong outlet stem 200, respectively, and pushes the dual lumen catheter 400 over the locking ridges 212 214 of the upper prong 210 and the locking ridges 222 224 of the lower prong 220. The taper that is incorporated in the upper and lower prongs 210 220 facilitates this operation. The practitioner then slides the locking collar 300 over the set of the locking ridges 222 224. The locking collar 300 is in the locked position when the locking collar 300 rests between the locking ridges 212 214 and the locking ridges 222 224. In the particular embodiment shown in FIG. 9A, the maximum ridge-to-ridge distance (measured from the midpoint of the locking ridges 212 214 of the upper prong 210 to the midpoint of the locking ridges 222 224 of the lower prong 220) is approximately 0.128 inches, and the interior width of the narrow waist 320 (including the ramps on either side of the midpoint of the locking collar 300) is also approximately 0.128 inches.

Figure 9B:
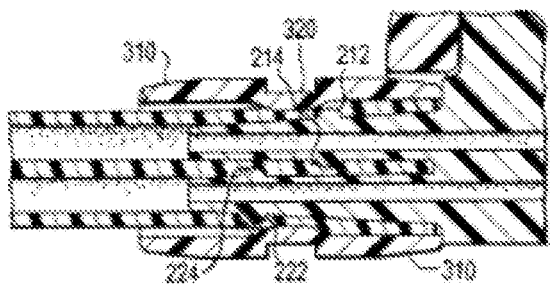
FIG. 9B is a cross-sectional side view of the catheter and locking collar attached to the dual prong outlet stem of the dual reservoir access port of FIG. 1, in accordance with an exemplary embodiment of the present invention.

FIG. 9B illustrates a cross-sectional side view of the dual lumen catheter 400 and locking collar 300 attached to the stem 200 of the dual reservoir access port 100, in accordance with an exemplary embodiment of the present invention. When the locking collar 300 is in the locked position, the upper and lower exterior locking ridges 212 222 compress the exterior wall 480 of the dual lumen catheter 400 against the interior of the locking collar 300, particularly against the narrow waist 320. The upper and lower interior locking ridges 214 224 compress the dividing wall 470 of the dual lumen catheter 400 against the opposite prong. In other words, the interior locking ridge 214 compresses the dividing wall 470 against the prong 220, and the interior locking ridge 224 compresses the dividing wall 470 against the prong 210. These multiple compression points contribute to create a fluid tight connection between the dual lumen catheter 400 and the dual reservoir access port 100.

In the embodiments shown in FIGS. 6, 7, and 9, the locking ridges 212 214 of the upper prong 210 are closer to the stem base 230, and the locking ridges 222 224 of the lower prong 220 are closer to the distal end 216 226 of the dual prong outlet stem 200. This configuration of locking ridges is for illustration purpose only, and does not limit the scope of the present invention. It is to be understood that the relative positions of the locking ridges of the upper prong and the locking ridges of the lower prong can be reversed and positioned anywhere along the length of the dual prong outlet stem.

Figure 10A:
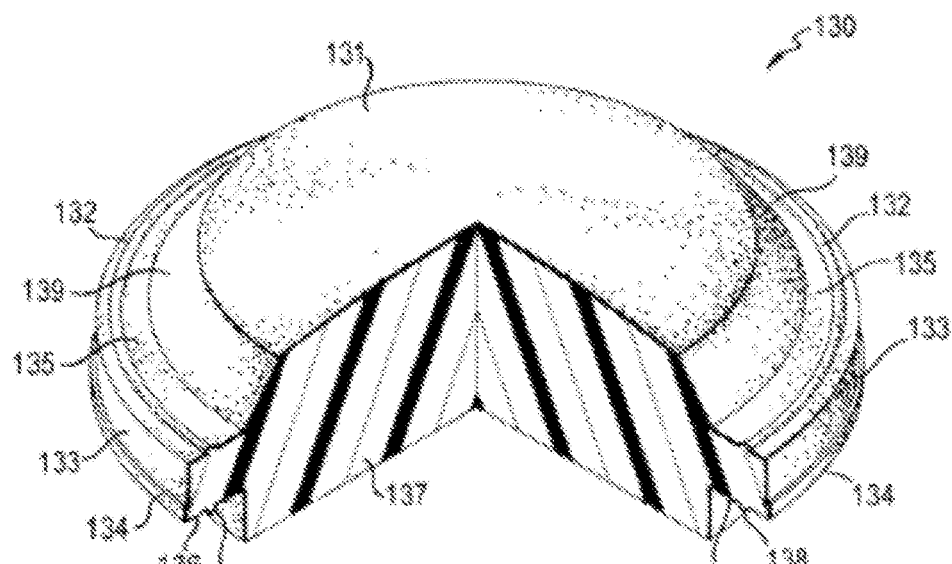
FIG. 10A is a cut away view of one embodiment of a septum used with the dual reservoir access port of FIG. 1, in accordance with an exemplary embodiment of the present invention.

FIG. 10A is a cut away view of one embodiment of an individual septum 130 used with an exemplary embodiment of the dual reservoir access port 100 of the present invention. The individual septum 130 comprises an upper dome 131, an upper compression zone 139, a flange 133, and a lower plug 137. The flange 133 comprises a flat upper surface 135 and a flat lower surface 136. In this particular embodiment, the flange 133 further comprises an upper sealing ring 132, a lateral sealing ring 134, and a bottom sealing ring 138. The upper and bottom sealing rings 132 138 are rounded ridges located respectively on the top and bottom surfaces 135 136 of the flange 133. The lateral sealing ring 134 is a thin strip surrounding the outer circumference of the flange 133. In the embodiment illustrated in FIG. 10A, the lateral sealing ring has a rectangular cross section. It is contemplated that septa with other shapes or configurations may be used with the present invention dual reservoir implantable port, as long as fluid tight seals can be formed atop the distal and proximal reservoirs.

Figure 10B:
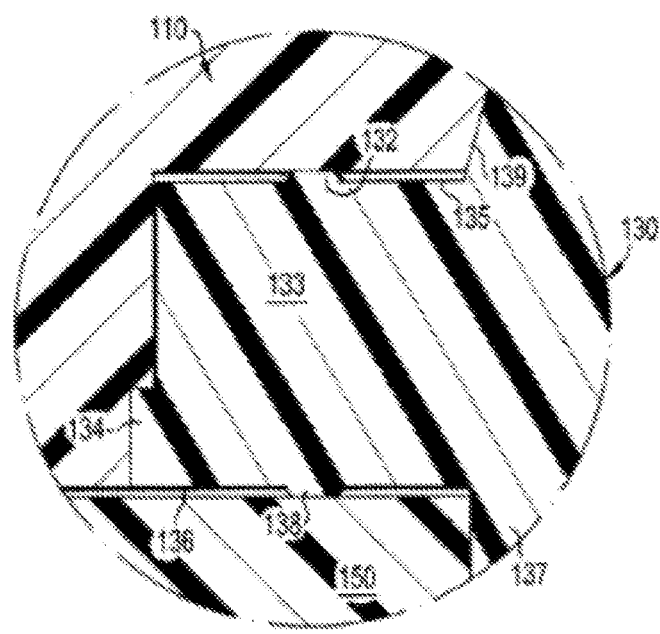
FIG. 10B is an enlarged cross-sectional view of an assembled cap, septum, and base portion of the dual reservoir access port of FIG. 1 indicated by portion J in FIG. 4A, in accordance with an exemplary embodiment of the present invention.

FIG. 10B is an enlarged cross-sectional view of portion J in FIG. 4A, illustrating a portion of the septum 130 assembled into the cap 110 and port base 150 of one embodiment of the dual reservoir access port 100, in accordance with an exemplary embodiment of the present invention. When the cap 110 is locked in place against the port base 150, the cap 110 compresses the individual septum 130 against the port base 150. The upper sealing ring 132 and the lateral sealing ring 134 of the septum 130 make contact with the cap 110 and deform to form fluid tight seals. The bottom sealing ring 138 makes contact with the top surface 154 of the port base 150, and deforms to make a fluid tight seal. The lower plug 137 also radially compresses against the sidewalls 152 158 of the respective distal and proximal reservoirs 151 157, further helping to seal the respective reservoirs.

Referring now to FIG. 11A there is illustrated an exemplary perspective view of alternative embodiment of the puncture shield 140, generally designated as 1100, in accordance with an exemplary embodiment of the present invention. The puncture shield 1100 comprises a pair of end portions 1120A and 1120B. The end portion 1120A comprises a lumen 1130A having a D-shaped cross-section 1160A, and the end portion 1120B comprises a lumen 1130B having a D-shaped cross-section 1160B.

The flat-side portions of the D-shaped portions 1120A and 1120B are seamlessly connected to one another by a flat planar portion 1110. Viewed another way, the puncture shield 1100 is a D-shaped tube with a semi-cylindrical portion removed to leave the flat planar portion 1110 and the end portions 1120A and 1120B.

Referring now to FIG. 11B, there is illustrated an exemplary cross-sectional view of an exemplary embodiment of the dual port 100, generally designated as 100', in which the puncture shield 140 is replaced with the puncture shield 1100, in accordance with an exemplary embodiment of the present invention. It is to be understood that like elements in FIGS. 1-3 and 5 are illustrated in FIG. 11B. The view in FIG. 11B is of a cross-section of the port 100' taken along a section line similar to the section line A-A illustrated in FIG. 2.

FIG. 11B illustrates that the puncture shield 1100 is disposed in the portion 164D of the base 150 underneath the bottom 153 of the distal reservoir 151 to prevent a needle 500 from penetrating the bottom of the reservoir 151 and entering the lower fluid channel 172. The puncture shield 1100 is also disposed between the bottom 153 of the distal fluid reservoir 151 and the second fluid pathway 174.

At least a portion 1144A of the puncture shield 1100 (corresponding to the portion 144A of the puncture shield 140) is disposed within the portion 164C of the lower fluid channel 172 directly underneath the distal reservoir 151. It is to be understood that the puncture shield 1100 may extend through the lower fluid channel 172 beyond the walls 152 of the distal fluid reservoir 151, such as through the portion 164D illustrated in FIGS. 5B-5C. It also is to be understood that the puncture shield 1100 can be of other sizes and shapes, such as C-shaped, stadium shaped, oval, triangular, rectangular, or trapezoidal, to match the lumens 172.1 and 172.3 if they are C-shaped, stadium shaped, oval, triangular, rectangular, or trapezoidal.

The puncture shield 1100 is formed from a material that is harder than the material forming the port base 150. More preferably, the material is one that, at a thin thickness, would withstand penetration by a infusion needle. In an exemplary embodiment, the puncture shield 1100 is a metal or metal alloy tube lining at least the portion 164C of the lower fluid channel 172 directly underneath the distal reservoir 151. In an exemplary embodiment, titanium is used for the construction of the puncture shield 1100. An exemplary wall thickness for such titanium tube puncture shield is approximately 0.005 inches. Other metals or metal alloys, e.g., stainless steel, may also be suitable for constructing the puncture shield.

With respect to FIGS. 11A and 11B together, the flat planar portion 1110 of the puncture shield 1100 comprises a width 1150 which is desirably greater than the width of the fluid channel 172 to ensure that the fluid channel 172 is fully covered to prevent a needle penetrating through the bottom of the reservoir 151 and into the fluid channel 172. The puncture shield 140 comprises a length 1140, which is desirably greater than the length of the portion 164C of the fluid channel 172.

At least three embodiments for the puncture shield 1100 lining the lower fluid channel 172 are contemplated. In one embodiment, the portion 164D of the lower fluid channel 172 in which the puncture shield 1100 is disposed is notched so that the inner lumen 1130A 1130B of the puncture shield 1100 in the end portions 1120A and 1120B has the same cross sections 1160A and 1160B as the cross section 172.4 of the inner lumen 172.3 of the lower fluid channel 172 in the portion 164E. The fluid channel 172 outside the portion 164D and the lumen 1130A 1130B of the puncture shield 1100 together form the lower, second fluid pathway 174, which comprises a lumen 174.1 having a cross section 174.2. In this embodiment, the cross section 174.2 of the effective fluid pathway 174 is the same at all points between the distal tip 226 and the opening 228, except in the portion between the end portions 1120A and 1120B because the lower portion of the notch portion 164D is not entirely filled by a corresponding portion of the puncture shield 1100.

In another embodiment, the portion 164D of the lower fluid channel 172 which is notched is shaped to match the shape of the puncture shield 1100. Thus, the cross section 174.2 of the effective fluid pathway 174 is the same at all points between the distal tip 226 and the opening 228 and is equal to the cross section 172.4. In yet another embodiment, the lower fluid channel 172 contains no notch. Thus, the cross section 172.2 is the same as the cross section 172.4 in the portion 164E. The cross section of the lower fluid channel 172 is constant along all lengths of the lower fluid channel 172 from the distal tip 226 to the opening 228. The puncture shield 140 is fitted in the lower fluid channel 172. Thus, the lumen 174.1 of the effective fluid pathway 174 has a slightly narrower cross section 174.2 where the puncture shield 1100 is disposed in the lower fluid channel 172.

Figure 12A:
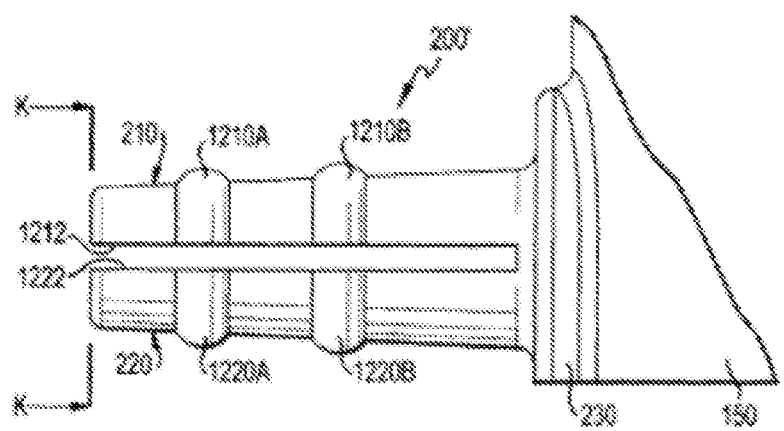
FIG. 12A illustrates an exemplary elevation view of a further exemplary embodiment of a dual prong outlet stem, in accordance with an exemplary embodiment of the present invention.

Referring now to FIG. 12A, there is illustrated an exemplary elevation view of an alternative exemplary embodiment of the stem 200, designated generally as 200', in accordance with an exemplary embodiment of the present invention. As can be seen in FIG. 12A, the upper prong 210 of the stem 200' comprises a first rounded locking ridge 1210A and a second locking ridge 1210B disposed around its exterior surface. The lower prong 220 comprises a first rounded locking ridge 1220A and a second rounded locking ridge 1210B disposed around its exterior surface. Interior flat surfaces 1212 and 1222 of the respective prongs 210 and 220 are smooth and contain no locking ridges.

Figure 12B:
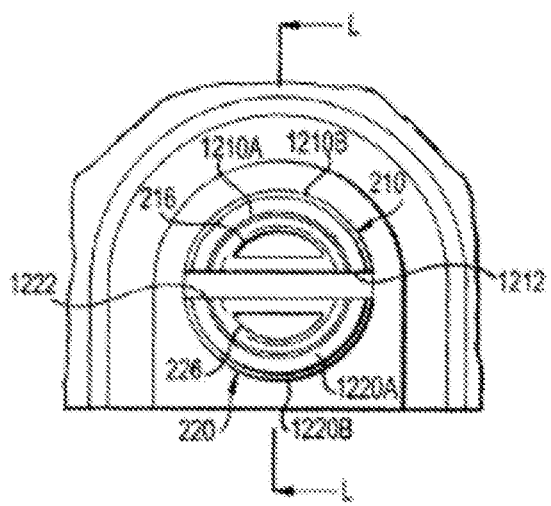
FIG. 12B illustrates an exemplary front, planar view of the exemplary dual prong outlet stem of FIG. 12A from a section line K-K illustrated in FIG. 12A, in accordance with an exemplary embodiment of the present invention.
Figure 12C:
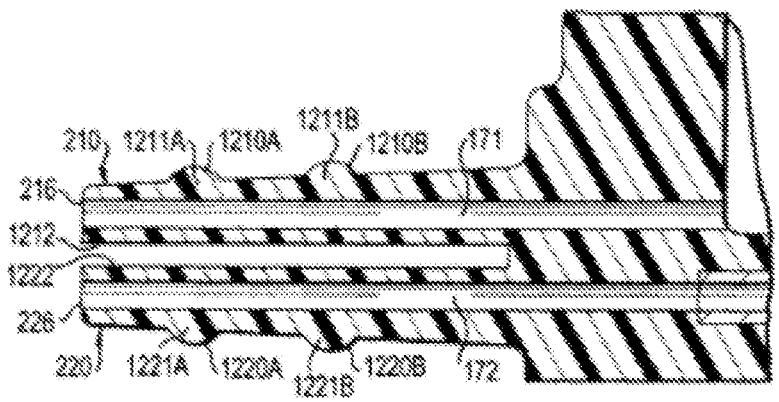
FIG. 12C illustrates an exemplary cross-sectional view of the exemplary dual prong outlet stem of FIG. 12A taken along a section line illustrated in FIG. 12B, in accordance with an exemplary embodiment of the present invention.

Referring now to FIG. 12B, there is illustrated a front, planar view of the stem 200' from a line K-K illustrated in FIG. 12A, in accordance with an exemplary embodiment of the present invention. FIG. 12C illustrates an exemplary cross-sectional view of the dual prong outlet stem 200' taken along a section line L-L shown in FIG. 12B, in accordance with an exemplary embodiment of the present invention. As illustrated in FIG. 12B, each of the upper and lower prongs 210 and 220 of the dual prong outlet stem 200' is of generally semicircular shape as is the case with the dual prong outlet stem 200.

FIGS. 12B and 12C together illustrate the locking ridges 1210 and 1220 of the upper and lower prongs 210 and 220 in further detail. Specifically, the locking ridges 1210A and 1210B are each an exterior, curved locking ridge located on the curved outer surface of the upper prong 210. Similarly, the locking ridges 1220A and 1220B are each an exterior, curved locking ridge located on the curved outer surface of the lower prong 220. None of the locking ridges 1210A and 1210B includes an interior, straight locking ridge located on the interior flat surface 1212 of the prong 210 facing the prong 220, and none of the locking ridges 1220A and 1220B includes an interior, straight locking ridge located on the interior flat surface 1222 of the prong 220.

The locking ridges 1210A and 1210B each have a semicircular cross section, as illustrated in FIG. 12C. Specifically, the locking ridge 1210A has a semi-circular cross section 1211A, and the locking ridge 1210B has a semi-circular cross section 1211B. Similarly, the locking ridges 1220A and 1220B each have a semi-circular cross section. Specifically, the locking ridge 1220A has a semi-circular cross section 1221A, and the locking ridge 1220B has a semi-circular cross section 1221B. The semi-circular cross sections 1211 and 1221 of the locking ridges 1210 and 1220 facilitate insertion of the catheter 400 onto the stem 200' as the catheter 400 passes over the rounded surfaces more easily than if the surfaces were barb-shaped. At the same time, the locking ridges 1210 and 1220 allow for the use of the locking collar 300 to secure the catheter 400 to the dual port 100. When slipped over the catheter 400 disposed on the stem 200', the narrow waist 320 of the locking collar 300 is disposed between the locking ridges 1210A and 1210B and between the locking ridges 1220A and 1220B.

The locking ridges 1210 of the upper prong 210 of the dual prong outlet stem 200' and the locking ridges 1220 of the lower prong 220 do not encircle the exterior circumference of the respective prong 210 and 220, unlike the locking ridges 212 and 222, as described above. The exterior, curved locking ridges 1210 of the upper prong 210 follow the curved contour of the exterior of the upper prong 210. As mentioned above, there is no corresponding interior, straight locking ridge on the flat inside surface 1212 of the upper prong 210. The exterior, curved locking ridges 1220 of the lower prong 220 follow the curved contour of the exterior of the lower prong 220. As mentioned above, there is no corresponding interior, straight locking ridge on the flat inside surface 1222 of the lower prong 220.

In the particular embodiment illustrated in FIGS. 12A-C, the upper and lower prongs 210 and 220 are slightly tapered on their exterior curved surfaces and also on the flat surfaces 1212 and 1222 that face each other. Because of the slight taper of the upper and lower prongs 210 and 220, the locking ridge 1210B of the upper prong 210 is of a slightly larger arc length than the locking ridge 1210A, and the locking ridge 1220B of the lower prong 220 is of a slightly larger arc length than the locking ridge 1220A. The upper and lower fluid channels 171 and 172 are of a generally constant size, i.e., cross section, throughout the length of the stem 200' despite the taper. The taper of the prongs 210 and 220 of the stem 200' facilitates insertion of the catheter 400 onto the stem 200'. The constant cross-sectional size of the fluid channels 171 and 172 facilitates proper flow characteristic during infusion.

The dual prong outlet stem 200 and 200' and the port base 150 may be made as a single piece or as separate pieces by molding or other suitable manufacturing techniques. If made as separate pieces, the dual prong outlet stem 200 or 200' and the port base 150 may be attached together through welding, solvent bonding, adhesion, or other suitable manufacturing methods. To manufacture the port base 150 via an injection molding process, a mold is formed and mandrels are inserted into the mold for the fluid channels 171 172. The puncture shield 140 or 1100 is disposed about the mandrel for the lower fluid channel 172. The material forming the port base is injected into the mold. The port base 150 is removed from the mold and mandrels, and the septa 130 are pressed into the reservoirs 151 and 157. The cap 110, molded separately, is snapped onto the port base 150. Preferably, the cap 110 is solvent bonded to the port base 150. The dual reservoir access port 100 or 100' is complete. Alternatively, the port base 150, the outlet stem 200 or 200', and the cap 110 may be formed integrally, e.g., injection molded using a collapsible core pin, or machined from a stock material.

In an exemplary embodiment, the dual reservoir access port 100 or 100' is formed from biocompatible plastic materials. The cap 110 and the port base 150 may be made from polysulfone resin or acetal plastic. The cap 110 and the port base 150 may be made from the same material or different materials. Additional suitable plastic materials, without limitation, are polyvinylchloride, polytetrafluoroethylene, polyetheresulfone, polyethylene, polyurethane, polyetherimide, polycarbonate, polyetheretherketone, polysulfone, polypropylene, and other similar compounds known to those skilled in the art. Each individual septum 130 is typically made from a silicone elastomer, such as polysiloxanes, and other similar compounds known to those skilled in the art.

In an exemplary embodiment, the dual lumen catheter 400 is formed from a biocompatible plastic or elastomer, preferably from a biocompatible elastomer. Suitable biocompatible plastics include materials such as, for example, polysiloxanes, silicone, polyurethane, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. Preferably, the dual lumen catheter 400 is formed from the elastomeric material such that they are flexible, durable, soft, and easily conformable to the shape of the area to be catheterized in a patient and minimize risk of harm to vessel walls. The dual lumen catheter 400 is preferably formed of a soft silicone or polyurethane elastomer which has a hardness of at least about 80-A on a Shore durometer scale. Such an elastomer can include radio opaque materials, such as 20% barium sulfate, in the elastomer to provide radiopacity.

In the particular embodiment shown in FIGS. 1 and 3, a cavity 501 is formed in the dividing wall 155 of the port base 150 between the reservoirs 151 and 157. The cavity 501 is sized to accommodate an identification device, preferably a Radio Frequency Identification (RFID) chip, such as a micro RFID manufactured by PositiveID Corporation. The identification device is preferably hermitically sealed, and stores information relevant to the implantable port. In an exemplary embodiment, an RFID chip is installed in the cavity 501, which provides a serial number of the device, date, and batch information, and identifies the port 100 as a dual reservoir access port 100 suitable for high pressure injections. Other information may also be encoded within the identification device. It is to be understood that the location of the cavity 501 may be anywhere within the implantable port, as long as it does not interfere with the functionality of the port.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention.

We claim:

1. A dual prong outlet stem, comprising:
   a first prong having a proximal end, a distal end, and a first distal tip having a first distal opening;
   a second prong having a proximal end, a distal end, and a second distal tip having a second distal opening;
   wherein:
      the dual prong outlet stem is capable of being bonded to an access port base having a first reservoir and a second reservoir, wherein the first distal opening is in fluid communication with the first reservoir of the access port base and the second distal opening is in fluid communication with the second reservoir of the access port;
      the first prong comprises one first locking ridge disposed on an exterior surface of the first prong, the second prong comprises one second locking ridge disposed on an exterior surface of the second prong, the one first locking ridge is offset from the one second locking ridge by an offset distance such that the one first locking ridge is at or near the proximal end of the first prong and the one second locking ridge is at or near the distal end of the second prong, wherein a dual lumen catheter can be secured to the dual prong outlet stem via a locking collar having a narrow waist, the narrow waist having a width approximately equal to or slightly shorter than the offset distance;
      the first prong has a length that is equal to a length of the second prong;
      the first prong has a semicircular cross section and the second prong has a semicircular cross section, wherein:
         the first prong has a first flat surface and a first curved surface which together form a first prong exterior circumference, the one first locking ridge protrudes from the first prong and entirely encircles the first prong exterior circumference;
         the second prong has a second flat surface and a second curved surface which together form a second prong exterior circumference, the one second locking ridge protrudes from the second prong and entirely encircles the second prong exterior circumference;
         each of the one first locking ridge and the one second locking ridge is rounded; and
         the first flat surface and the second flat surface face each other.

2. The dual prong outlet stem recited in claim 1, wherein the first distal opening provides a first fluid pathway that has a constant cross section, and the second distal opening provides a second fluid pathway that has a constant cross section.

3. The dual prong outlet stem recited in claim 1, wherein at least one of the one first locking ridge and the one second locking ridge has a semicircular cross section.

4. The dual prong outlet stem recited in claim 1, wherein the first curved surface and the first flat surface of the first prong exhibit a taper toward the first distal tip and the second curved surface and the second flat surface of the second prong exhibit a taper toward the second distal tip.

5. A dual prong outlet stem adapted for use with an access port, comprising:
   a first prong having a proximal end and a distal end;
   a second prong having a proximal end and a distal end; and,
   a symmetrical locking collar comprising a first hollow section, a second hollow section, and a narrow waist section there-between, wherein the symmetrical locking collar can be placed onto the dual prong outlet stem in either direction;
   wherein the dual prong outlet stem is designed to receive a dual lumen catheter, and the locking collar secures the dual lumen catheter to the dual prong outlet stem,
   wherein the first prong comprises one first locking ridge disposed on an exterior surface of the first prong, the second prong comprises one second locking ridge disposed on an exterior surface of the second prong, the one first locking ridge is offset from the one second locking ridge by an offset distance such that the one first locking ridge is at or near the proximal end of the first prong and the one second locking ridge is at or near the distal end of the second prong, wherein the narrow waist section of the symmetrical locking collar is positioned within the offset distance when the dual lumen catheter is secured to the dual prong outlet stem;
   wherein the first prong has a length that is equal to a length of the second prong;
   wherein the first prong has a semicircular cross section and the second prong has a semicircular cross section, wherein:
      the first prong has a first flat surface and a first curved surface which together form a first prong exterior circumference, the one first locking ridge protrudes from the first prong and entirely encircles the first prong exterior circumference;
      the second prong has a second flat surface and a second curved surface which together form a second prong exterior circumference, the one second locking ridge protrudes from the second prong and entirely encircles the second prong exterior circumference;
      each of the one first locking ridge and the one second locking ridge is rounded; and
      the first flat surface and the second flat surface face each other.

6. The assembly recited in claim 5, wherein a first distal opening provides a first fluid pathway that has a constant cross section, and a second distal opening provides a second fluid pathway that has a constant cross section.

7. The assembly recited in claim 5, wherein the first hollow section is cylindrical and the second hollow section is cylindrical.

8. The assembly recited in claim 5, wherein the locking collar is symmetrical about a middle point of the narrow waist section, wherein the first hollow section and the second hollow section have identical exterior and interior dimensions, wherein the narrow waist section is symmetrical about the middle point.

9. The assembly recited in claim 8, wherein in a locked configuration, the narrow waist section of the symmetrical locking collar locates between the one first locking ridge and the one second locking ridge, and the first hollow section and the second hollow section of the symmetrical locking collar enclose the one first locking ridge and the one second locking ridge.

10. The assembly recited in claim 5, wherein: the narrow waist section has a waist inner diameter, the first hollow section has a first section inner diameter, and the second hollow section has a second section inner diameter; and, the first section inner diameter at a first hollow section end and the second section inner diameter at a second hollow section end are each larger than the waist inner diameter.

11. The assembly recited in claim 10, wherein the first section inner diameter gradually narrows from the first hollow section end to the narrow waist section to match the waist inner diameter, and the second section inner diameter gradually narrows from the second hollow section end to the narrow waist section to match the waist inner diameter.

12. An access port base, comprising:
a proximal end having a proximal fluid reservoir;
a distal end having a distal fluid reservoir;
a first fluid pathway in fluid communication with the distal fluid reservoir;
a second fluid pathway in fluid communication with the proximal fluid reservoir; and,
a dual prong outlet stem projecting from the distal end, the dual prong outlet stem comprising:
a first prong having a proximal end and a distal end, the first prong comprising a first distal tip having a first distal opening, wherein the first distal opening is in fluid communication with the first fluid pathway;
a second prong having a proximal end and a distal end, the second prong comprising a second distal tip having a second distal opening, wherein the second distal opening is in fluid communication with the second fluid pathway;
wherein the first prong comprises one first locking ridge disposed on an exterior surface of the first prong, the second prong comprises one second locking ridge disposed on an exterior surface of the second prong, the one first locking ridge is offset from the one second locking ridge by an offset distance such that a dual lumen catheter can be secured to the dual prong outlet stem via a locking collar having a narrow waist, the narrow waist having a width approximately equal to or slightly shorter than the offset distance;
wherein the one first locking ridge is at or near the proximal end of the first prong and the one second locking ridge is at or near the distal end of the second prong;
wherein the first prong has a length that is equal to a length of the second prong;
wherein the first prong has a semicircular cross section and the second prong has a semicircular cross section, wherein:
the first prong has a first flat surface and a first curved surface which together form a first prong exterior circumference, the one first locking ridge protrudes from the first prong and entirely encircles the first prong exterior circumference;
the second prong has a second flat surface and a second curved surface which together form a second prong exterior circumference, the one second locking ridge protrudes from the second prong and entirely encircles the second prong exterior circumference;
each of the one first locking ridge and the one second locking ridge is rounded; and
the first flat surface and the second flat surface face each other.

13. The access port base recited in claim 12, wherein the distal fluid reservoir, the proximal fluid reservoir, and the dual prong outlet stem are arranged in-line with each other.

14. The access port base recited in claim 12, wherein the first prong, the second prong, the first fluid pathway, and the second fluid pathway are stacked with at least one of a horizontal offset and vertical offset with respect to each other.

* * * * *

UNITED STATES PATENT AND TRADEMARK OFFICE
CERTIFICATE OF CORRECTION

PATENT NO. : 10,485,964 B2
APPLICATION NO. : 15/212725
DATED : November 26, 2019
INVENTOR(S) : Christopher Linden et al.

Page 1 of 1

It is certified that error appears in the above-identified patent and that said Letters Patent is hereby corrected as shown below:

In the Specification

In Column 1, Line 7, delete "divisional" and insert -- continuation --, therefor.

In Column 5, Line 36, after "line" insert -- L-L --.

In Column 5, Line 56, delete "aesthetics.\" and insert -- aesthetics. --, therefor.

In Column 12, Line 61, after "leaking" insert -- . --.

In Column 15, Line 63, delete "he" and insert -- the --, therefor.

In Column 20, Line 26, delete "polyetheresulfone," and insert -- polyethersulfone, --, therefor.

Signed and Sealed this
Fourth Day of February, 2020

Andrei Iancu
*Director of the United States Patent and Trademark Office*